(12) United States Patent
Wilson et al.

(10) Patent No.: US 8,704,124 B2
(45) Date of Patent: Apr. 22, 2014

(54) LOW TEMPERATURE ENCAPSULATE WELDING

(75) Inventors: Darren James Wilson, York (GB); Nicholas S. Ritchey, Collierville, TN (US); Stephen James Guy Taylor, Middlesex (GB)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/146,988

(22) PCT Filed: Jan. 29, 2010

(86) PCT No.: PCT/US2010/022606
§ 371 (c)(1),
(2), (4) Date: Sep. 23, 2011

(87) PCT Pub. No.: WO2010/088531
PCT Pub. Date: Aug. 5, 2010

(65) Prior Publication Data
US 2012/0010709 A1    Jan. 12, 2012

Related U.S. Application Data

(60) Provisional application No. 61/148,283, filed on Jan. 29, 2009.

(51) Int. Cl.
*B23K 26/00* (2006.01)

(52) U.S. Cl.
USPC .................................. 219/121.64; 623/16.11

(58) Field of Classification Search
USPC ................... 219/121.64; 623/16.11; 29/592.1
See application file for complete search history.

(56) References Cited

U.S. PATENT DOCUMENTS

| 4,361,153 A | 11/1982 | Slocum et al. |
| 4,441,498 A | 4/1984 | Nordling |

(Continued)

FOREIGN PATENT DOCUMENTS

| EP | 1366712 | 12/2003 |
| EP | 1704893 | 9/2006 |

(Continued)

OTHER PUBLICATIONS

Authorized Officer BAE, Yeo Wool, International Search Report/Written Opinion in PCT/US2010/022606, mailed Oct. 7, 2010 (10 pages).

(Continued)

*Primary Examiner* — Dana Ross
*Assistant Examiner* — John Wasaff
(74) *Attorney, Agent, or Firm* — Fish & Richardson P.C.

(57) ABSTRACT

A load-bearing medical implant is disclosed that includes a load-bearing structure with a cavity extending into the outer surface of the structure. The cavity accommodates a sensor that is held in a fixed position within the cavity by an encapsulant. The cavity is covered by a plate that is welded over the cavity in close proximity to the sensor and encapsulant to provide a seal over the cavity and the electronic component without causing thermal damage to the encapsulant or sensor despite the close proximity of the encapsulant and sensor to the welded areas of the plate and structure. Methods for encapsulating the sensor in the cavity, methods for encapsulating a wire bus leading from the sensor through a channel in the implant and methods for pulsed laser welding of weld plate over the sensor and encapsulant with thermal damage to either are disclosed.

31 Claims, 18 Drawing Sheets

(56) References Cited

U.S. PATENT DOCUMENTS

| | | |
|---|---|---|
| 4,494,545 A | 1/1985 | Slocum et al. |
| 4,991,582 A | 2/1991 | Byers et al. |
| 5,330,477 A | 7/1994 | Crook |
| 5,423,334 A | 6/1995 | Jordan |
| 5,720,746 A | 2/1998 | Soubeiran |
| 5,735,887 A | 4/1998 | Barreras et al. |
| 5,833,603 A | 11/1998 | Kovacs et al. |
| 5,836,989 A | 11/1998 | Shelton |
| 5,944,745 A | 8/1999 | Rueter |
| 6,009,878 A | 1/2000 | Weijand et al. |
| 6,011,993 A | 1/2000 | Tziviskos et al. |
| 6,034,296 A | 3/2000 | Elvin et al. |
| 6,051,017 A | 4/2000 | Loeb et al. |
| 6,120,502 A | 9/2000 | Michelson |
| 6,200,265 B1 | 3/2001 | Walsh et al. |
| 6,201,980 B1 | 3/2001 | Darrow et al. |
| 6,402,689 B1 | 6/2002 | Scarantino et al. |
| 6,411,854 B1 * | 6/2002 | Tziviskos et al. ............... 607/57 |
| 6,447,448 B1 | 9/2002 | Ishikawa et al. |
| 6,449,508 B1 | 9/2002 | Sheldon et al. |
| 6,477,424 B1 | 11/2002 | Thompson et al. |
| 6,499,488 B1 | 12/2002 | Hunter et al. |
| 6,535,766 B1 | 3/2003 | Thompson et al. |
| 6,539,253 B2 | 3/2003 | Thompson et al. |
| 6,567,703 B1 | 5/2003 | Thompson et al. |
| 6,636,769 B2 | 10/2003 | Govari et al. |
| 6,638,231 B2 | 10/2003 | Govari et al. |
| 6,641,540 B2 | 11/2003 | Fleischman et al. |
| 6,652,464 B2 | 11/2003 | Schwartz et al. |
| 6,658,300 B2 | 12/2003 | Govari et al. |
| 6,682,490 B2 | 1/2004 | Roy et al. |
| 6,706,005 B2 | 3/2004 | Roy et al. |
| 6,712,778 B1 | 3/2004 | Jeffcoat et al. |
| 6,749,568 B2 | 6/2004 | Fleischman et al. |
| 6,764,446 B2 | 7/2004 | Wolinsky et al. |
| 6,766,200 B2 | 7/2004 | Cox |
| 6,783,499 B2 | 8/2004 | Schwartz |
| 6,793,659 B2 | 9/2004 | Putnam |
| 6,804,552 B2 | 10/2004 | Thompson et al. |
| 6,810,753 B2 | 11/2004 | Valdevit et al. |
| 6,821,299 B2 | 11/2004 | Kirking et al. |
| 6,855,115 B2 | 2/2005 | Fonseca et al. |
| 6,895,280 B2 | 5/2005 | Meadows |
| 6,895,281 B1 | 5/2005 | Amundson et al. |
| 6,926,670 B2 | 8/2005 | Rich et al. |
| 6,939,299 B1 | 9/2005 | Petersen et al. |
| 6,968,743 B2 | 11/2005 | Rich et al. |
| 7,027,871 B2 | 4/2006 | Burnes et al. |
| 7,097,662 B2 | 8/2006 | Evans |
| 7,147,604 B1 | 12/2006 | Allen et al. |
| 7,182,736 B2 | 2/2007 | Roy |
| 7,190,273 B2 | 3/2007 | Liao et al. |
| 7,195,645 B2 | 3/2007 | DiSilvestro et al. |
| 7,209,790 B2 | 4/2007 | Thompson et al. |
| 7,212,133 B2 | 5/2007 | Goetz et al. |
| 7,218,232 B2 | 5/2007 | DiSilvestro |
| 7,229,415 B2 | 6/2007 | Schwartz |
| 7,256,695 B2 | 8/2007 | Hamel |
| 7,357,037 B2 | 4/2008 | Hnat et al. |
| 7,358,461 B2 | 4/2008 | Sone et al. |
| 7,381,223 B2 | 6/2008 | Kovacevic |
| 7,729,758 B2 | 6/2010 | Haller et al. |
| 7,756,579 B2 | 7/2010 | Nitzan et al. |
| 2001/0039374 A1 | 11/2001 | Schulman |
| 2002/0049394 A1 * | 4/2002 | Roy et al. ...................... 600/594 |
| 2002/0151978 A1 | 10/2002 | Zacouto et al. |
| 2003/0136417 A1 | 7/2003 | Fonseca |
| 2003/0143775 A1 | 7/2003 | Brady |
| 2003/0229381 A1 | 12/2003 | Hochmair et al. |
| 2004/0073221 A1 | 4/2004 | Biscup |
| 2004/0077073 A1 | 4/2004 | Schindler et al. |
| 2004/0094613 A1 | 5/2004 | Shiratori et al. |
| 2004/0113790 A1 | 6/2004 | Hamel et al. |
| 2004/0176815 A1 | 9/2004 | Janzig et al. |
| 2005/0010299 A1 | 1/2005 | Disilvestro et al. |
| 2005/0010300 A1 | 1/2005 | Disilvestro et al. |
| 2005/0010301 A1 | 1/2005 | Disilvestro et al. |
| 2005/0012617 A1 | 1/2005 | DiSilvestro et al. |
| 2005/0015014 A1 | 1/2005 | Fonseca et al. |
| 2005/0061079 A1 | 3/2005 | Schulman |
| 2005/0113932 A1 | 5/2005 | Kovacevic |
| 2005/0131397 A1 | 6/2005 | Levin |
| 2005/0187482 A1 | 8/2005 | O'Brien et al. |
| 2005/0194174 A1 | 9/2005 | Hipwell, Jr. et al. |
| 2006/0043178 A1 | 3/2006 | Tethrake et al. |
| 2006/0084997 A1 * | 4/2006 | Dejardin ..................... 606/62 |
| 2006/0095135 A1 | 5/2006 | Kovacevic |
| 2006/0111291 A1 | 5/2006 | DiMauro et al. |
| 2006/0131302 A1 | 6/2006 | Sone |
| 2006/0142656 A1 | 6/2006 | Malackowski et al. |
| 2006/0174712 A1 | 8/2006 | O'Brien et al. |
| 2006/0177956 A1 | 8/2006 | O'Brien et al. |
| 2006/0200030 A1 | 9/2006 | White et al. |
| 2006/0200031 A1 | 9/2006 | White et al. |
| 2006/0235310 A1 | 10/2006 | O'Brien et al. |
| 2006/0241354 A1 | 10/2006 | Allen |
| 2006/0283007 A1 | 12/2006 | Cros et al. |
| 2006/0287602 A1 | 12/2006 | O'Brien et al. |
| 2006/0287700 A1 | 12/2006 | White et al. |
| 2007/0090543 A1 | 4/2007 | Condie et al. |
| 2007/0123938 A1 | 5/2007 | Haller et al. |
| 2008/0161729 A1 | 7/2008 | Bush |
| 2008/0208516 A1 | 8/2008 | James |
| 2008/0300597 A1 * | 12/2008 | Morgan et al. .................. 606/62 |
| 2009/0222050 A1 | 9/2009 | Wolter et al. |
| 2010/0152621 A1 | 6/2010 | Janna et al. |

FOREIGN PATENT DOCUMENTS

| | | |
|---|---|---|
| WO | WO9626678 | 9/1996 |
| WO | WO9629007 | 9/1996 |
| WO | WO9720512 | 6/1997 |
| WO | WO9843701 | 10/1998 |
| WO | WO0019888 | 4/2000 |
| WO | WO0030534 | 6/2000 |
| WO | WO02056763 | 7/2002 |
| WO | WO02058551 | 8/2002 |
| WO | WO02061705 | 8/2002 |
| WO | WO2004005872 | 1/2004 |
| WO | WO2004014456 | 2/2004 |
| WO | WO2004052453 | 6/2004 |
| WO | WO2004052456 | 6/2004 |
| WO | WO2005007025 | 1/2005 |
| WO | WO2005013851 | 2/2005 |
| WO | WO2005039440 | 5/2005 |
| WO | WO2005084544 | 9/2005 |
| WO | WO2006010037 | 1/2006 |
| WO | WO2006052765 | 5/2006 |
| WO | WO2006055547 | 5/2006 |
| WO | WO2006063156 | 6/2006 |
| WO | WO2006086113 | 8/2006 |
| WO | WO2006086114 | 8/2006 |
| WO | WO2006089069 | 8/2006 |
| WO | WO2006094273 | 9/2006 |
| WO | WO2006110798 | 10/2006 |
| WO | WO2006131302 | 12/2006 |
| WO | WO2007002185 | 1/2007 |
| WO | WO2007002224 | 1/2007 |
| WO | WO2007002225 | 1/2007 |
| WO | WO2007009088 | 1/2007 |
| WO | WO2007025191 | 3/2007 |
| WO | WO2007061890 | 5/2007 |
| WO | WO2008105874 | 9/2008 |

OTHER PUBLICATIONS

Arms, S.W., et al., "Wireless Strain Measurement Systems—Applications and Solutions," presented at NSF-ESF Joint Conference on Structural Health Monitoring, Strasbourg, France, Oct. 3-5, 2003.

Bergmann, et al., "Hip joint loading during walking and running, measured in two patients", J Biomech, Aug. 1993;26(8):969-90.

Bergmann, et al., "Multichannel Strain Gauge Telemetry for Orthopaedic Implants", Technical Note, J. Biomechanics, vol. 21, No. 2, pp. 169-176, 1988.

(56) References Cited

OTHER PUBLICATIONS

Burny, et al., "Concept, design and fabrication of smart orthopaedic implants", Medical Engineering & Physics 22 (2000), pp. 469-479.
Carlson, et al, "A look at the prosthesis-cartilage interface: design of a hip prosthesis containing pressure transducers", J Biomed Mater Res. 1974; 8(4 pt 2): 261-269.
Carlson, et al., "A Radio Telemetry Device for Monitoring Cartilage Surface Pressures in the Human Hip", IEEE Trans. on Biomed. Engrg.,vol. BME-21, No. 4, pp. 257-264, Jul. 1974.
Clyde Church, "Radio Frequency Identification (RFID) Tracking of Orthopaedic Inventories Fact or Fiction, Today and Tomorrow," BONE Zone, Spring 2004, pp. 35-40.
D'Lima et al., "An implantable telemetry device to measure intra-articular tibial forces", J Biomech Feb. 2005; 38(2): pp. 299-304.
Fernald, et al., "A System Architecure for Intelligent Implantable Biotelemetry Instruments", Proc. IEEE Eng in Medicine and Biology Soc. Annual Conf., pp. 1411-1412, 1989.
Graichen, et al., "Four-channel telemetry system for in vivo measurement of hip joint forces", J Sioment Eng, Sep. 1991;13(5):370-4.
Graichen, et al., "Hip endoprosthesis for in vivo measurement of joint force and temperature", J Biomech Oct. 1999;32(10):1113-7.
Heinlein, et al., "An instrumented knee endoprothesis for measuring loads in vivo", EORS 2004, 51st Annual Meeting of the Orthopaedic research Society, Aug. 2007, 1 page.
Hodge, et al., "Contact Pressures in the Human Hip Joint Measured in Vivo", Proc. of National Academy of Science, U.S.A., No. 83, pp. 2879-2883, 1986.
Krebs et al., "Hip Biomechanics during Gait", J Orthop & Sports Phys Ther. Jul. 1998;28(1):51-9.
Kummer, F. J., et al., "Development of a Telemeterized Should Prothesis," Clin Orthop Relat Res., Sep. 1996 (330):31-4.
McGibbon, et al., "Cartilage degeneration in relation to repetitive pressure: case study of a unilateral hip hemiarthroplasty patient". J Arthroplasty, Jan. 1999, 14(1):52-8.
Morrell, et al., "Corroboration of in vivo cartilage pressures with implacations for synovial joint tribology and . . . ", Proc Natl Acad Sci USA, Oct. 11, 2005; 102(41):14819-24.
Park, et al, "Hip muscle co-contraction: evidence from concurrent in vivo pressure measurement and force estimation", Gait Posture. Dec. 1999;10(3):221-22.
Puers, et al., "A telemetry system for the detection of hip prosthesis loosening by vibration analysis", Sensors and Actuators 85 (2000) 42-47.
Global market for RFID in healthcare 2006-2016 by value: Source: IDTechEx, RFID in Healthcare 2006-2016, May 1, 2006.
Rohlmann, et al., "In vitro load measurement using an instrumented spinal fixation device", Medical Engineering & Physics, vol. 18, Issue 6, Sep. 1996, pp. 485-488.
Rohlmann, et al., "Loads on an internal spinal fixation device during walking", J Biomech, 1997; 30:41-47.
Rohlmann, et al., "Telemeterized Load Measurement Using Instrumented Spinal Internal Fixators in a Patient with Degenerative Instability", Spine, vol. 20, No. 24, 1995.
Rydell, "Forces Acting on the Femoral Head Prosthesis", Acta Orthop Scand, Suppl. 88, 1966.
Schneider, et al, "Loads acting in an intramedullary nail during fracture healing in the human femure", Journal of Biomechanics 34, 2001, pp. 849-857.
Taylor, S.J.G., Walker, P.S., Perry, J.S., Cannon, S.R., and Woledge, R., "The Forces in the Distal Femur and the Knee During Walking and Other Activities Measured by Telemetry," The Journal of Arthroplasty, 13, 428-437, 1998.
Taylor, et al., "Telemetry of forces from proximal femoral replacements and relevance to fixation", J Biomech. 1997; 30:225-234.
Townsend, et al., "Remotely powered multichannel microprocessor based telemetry systems for smart implantable devices and smart structures," Proc. SPIE vol. 3673, pp. 150-156 (Mar. 1999).
Westerhoff, P., "An Instrumented Implant for in vivo Measurement of Contact Forcdes and Contact Moments in the Shoulder Joint," Medical Engineering & Physics, 31 (2009) 207-213.
Yang, G.Y., et al, "Design of Microfabricated Strain Gauge Array to Monitor Bone Deformation in Vitro and in Vivo," Proceedings of the Fourth IEEE Symposium on Bioinformatics and Bioengineering, May 19-21, 2004, 8 pages.

\* cited by examiner

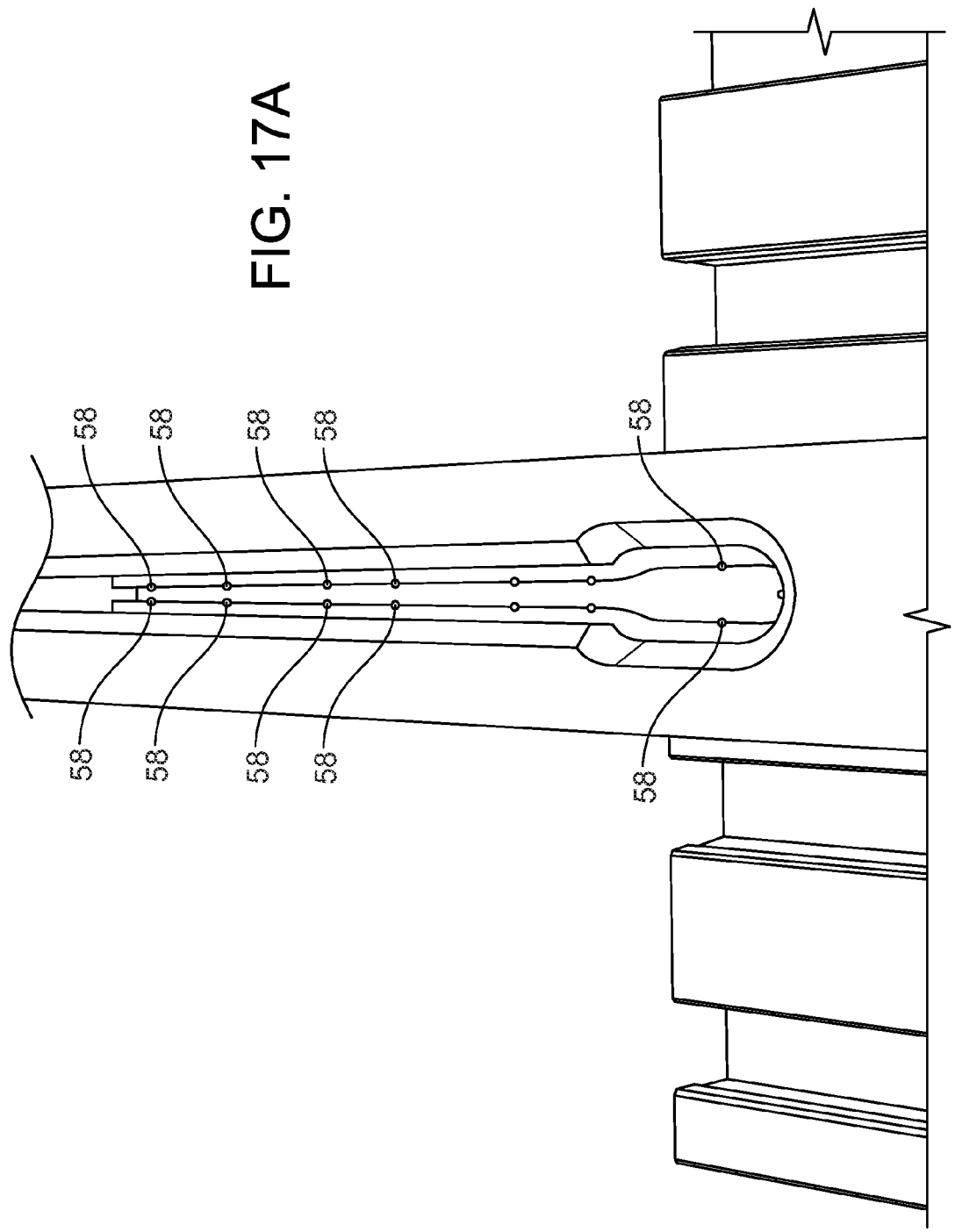

LOW TEMPERATURE ENCAPSULATE WELDING

CROSS-REFERENCE TO RELATED APPLICATIONS

This application claims the benefit of U.S. Provisional Application No. 61/148,283, filed 29 Jan. 2009. The disclosure of this prior application is incorporated by reference in its entirety.

BACKGROUND

1. Technical Field

This disclosure relates to various load-bearing medical implants with at least one electronic component that is sealed within a load-bearing structure of the implant to provide an impermeable barrier to protect the electronic component from body fluids. Various methods are disclosed for hermetically sealing the electronic component within a metallic load-bearing implant structure by welding a weld plate over the cavity that accommodates the electronic component without causing thermal damage to the encapsulant or electronic component. Various techniques are also disclosed for encapsulating an electronic component within a cavity of a load-bearing implant, such as an IM nail that includes one or more electronic sensors for landmark identification. The encapsulation and welding techniques disclosed herein address the problems associated with load-bearing implants having shallow cavities for sensor or other components and shallow channels for wiring, wherein the sensor and encapsulant can be damaged by welding a cover plate in close proximity to the enscapsulant and sensor.

2. Description of the Related Art

While most orthopedic implant developers are focused on improving current technologies, a handful are directed to developing "smart" or "intelligent" orthopedic implants equipped with implantable electronic components. Such electronically-equipped orthopedic implants provide real-time feedback to researchers, physicians or patients regarding how the implants are performing once they are placed inside a bone or joint. For example, orthopedic implants with electronic components can be used to detect poor bone in-growth, educate patients about safe post-operative activities, and improve surgical techniques.

The implantable electronic circuits and components must be small to minimize the size of the implant and designed to last in a physiological environment for an extended period of time. A reliable hermetic barrier must be used to preventingress of body fluids to the implantable electronic components and to assure long term biocompatibility. Generally used methods for protecting electronic circuits from the bodily fluids or other damaging environments include both hermetic sealing and polymer encapsulation.

Encapsulants, such as silicone elastomers, polyurethanes, silicone-urethane copolymer, polytetrafluoroethylene and epoxies have been used with implantable neuromuscular stimulators which rely on relatively simple circuits. However, polymers do not provide an impermeable barrier and therefore cannot be used for encapsulation of high density, high impedance electronic circuits. The moisture ingress will ultimately reach the electronic component resulting in electric shorting and degradation of leakage-sensitive circuitry.

For radio frequency powered electronic components disposed within a medical implant, a combination of hermetic packaging and polymer encapsulation are used. Hermetic packaging, using metals, ceramics or glasses, provides the implant electronic circuitry with a long term protection from the ingress of body fluids. The primary role of the encapsulant is to stabilize the electronic components by acting as stress-relieving shock and vibration absorbers and providing electrical insulation. Electrical signals, such as power and stimulation, enter and exit the implant through hermetic through-holes, which are hermetically welded into the implant walls. The through-hole assembly utilizes a ceramic or glass insulator to allow one or more wires to exit the implant.

In certain situations, electrical through-holes are not practical due to limited design space (e.g., <1 mm diameter) available for the parts in combination with the risk of fatigue failure of the connection due to cyclic loading of the implant. As a result, the role of the encapsulant as a secondary barrier to body fluid ingress becomes more important. Such devices include intramedullary (IM) nails, plates, rods and pedicle screws for orthopedic trauma application. In order to increase the body fluid barrier characteristics of the flexible impermeable encapsulant, the cavities that hold the electronic components need to be completely filled. This is difficult to achieve if the weld plate components have to be welded in close proximity with the encapsulant and the cavities are too long and narrow to allow adequate backfilling after hermetic sealing.

Currently available medical grade silicone encapsulants are only suitable for short-term (e.g., <30 days) implantable applications, referred to as "restricted grade." However, some materials, such as MED3-4213 and ELAST-EON™ developed by NuSil Silicone Technology (www.nusil.com) and AorTech (www.AorTech.com) respectively are unrestricted grades of silicone for long term implantation. Given that the onset temperature of thermal degradation for these types of materials is approximately 230° C., standard welding techniques, which generate local temperatures in the 400° C.-600° C. range, are not appropriate without the risk of degradation of either mechanical or optical properties the silicone. When exposed to high temperature conditions, the silicone will degrade leading to unpredictable performance.

Scanning electron microscope (SEM) micrographs of cured MED3-4213 encapsulated in an implant before and after conventional welding techniques are shown in FIGS. 1A-1E. It is evident from FIGS. 1A-1E that performance degradation resulting from increases in optical absorption are noticeable in the form of a hazy or milky appearance that is apparent from a comparison of FIG. 1A, which shows a layer of undamaged silicone, and FIGS. 1B-1E. Furthermore, mechanical degradation takes the form of voids 22 (FIG. 1B), pitting 23 (FIG. 1C), degraded portions 24 of the polymer near the welding zones 25 (FIGS. 1D-1E), hardening/denaturizing, out gassing of volatiles, brittle structures, crazing, cracking, shrinking, melting, or delamination. Accordingly, all of these problems compromise biocompatibility and mechanical performance of the implant.

There are no existing medical grade elastomers that can meet the high temperatures (400° C.-600° C.) needed for conventional welding which is used to provide a hermetic seal in the form of a weld plate over the cavity accommodating electronic component. As a result, a more cost-effective solution would be to optimize the existing methods of hermetic sealing. Consequently, there is a need for improved methods of packaging electronic components within an encapsulant that overcomes the thermal degradation issue caused by conventional welding techniques used to provide a hermetic seal. This need applies to medical implants and other unrelated applications.

SUMMARY OF THE DISCLOSURE

A load-bearing medical implant is disclosed that comprises a metallic load-bearing structure. The load-bearing structure comprises an outer surface and a cavity extending into the outer surface. The cavity accommodates an electronic component that is held in a fixed position in the cavity by an encapsulant. The cavity is covered by a plate that is welded over the cavity in close proximity to the electronic component and encapsulant to provide a seal over the cavity and the electronic component.

In a refinement, the encapsulant is substantially free of thermal damage despite the close proximity of the encapsulant to the welded plate.

In another refinement, the barrier is a silicone encapsulant that is temperature stable below about 150°. In a further refinement of this concept, the silicone encapsulant fills the cavity without substantial void spaces.

In another refinement, the load-bearing structure may also include a channel that extends from the cavity and along the outer surface of the structure. In such a refinement, the channel can be used to accommodate a wire, wire bundle or wire bus connected to the electronic component. In such an embodiment, the wire may extend through the channel and outside the implant as the encapsulant is used to form a barrier that prevents body fluids from entering the cavity and reaching the electronic component.

In a refinement, a single plate is also welded over the channel and the cavity without damage to the encapsulant or electronic component.

In another refinement, the metallic load-bearing structure further comprises a landmark, such as a screw hole of an IM nail, and the electronic component is a spatial sensor used to identify a location of the landmark in a patient's body during installation of the IM nail.

In designing the IM nails and implants discussed above, special attention is paid to the issue of potential damage to the encapsulant and possibly the sensor for implants that have shallow cavities for the sensor and shallow channels for the wiring or wire bus. Damage to the encapsulant and possibly the sensor becomes an issue as the welding area is in close proximity to the encapsulant and sensor.

Therefore, techniques are disclosed for encapsulating an electronic component within a cavity of a load-bearing implant that must also be welded. The disclosed techniques may include one or more of the following concepts: (a) post-curing treatment of the encapsulant to minimize the thermal degradation of the encapsulant during the welding process; (b) encapsulation techniques that reduce or eliminate void spaces in the encapsulant or cavity for long-term protection of the electronic component from body fluids; (c) optimization of the laser welding conditions such as pulse energy, duration, and repetition rate, traverse speed, degree of overlap of the of the laser weld spots during pulse mode and penetration of the weld spots to limit the exposure of the encapsulant to heat; (d) improved designs of the weld plate geometry and cavity assembly; and (e) application of heat sinks to limit the heat transferred from the weld location to the encapsulant.

In one disclosed method, a hermetic seal is formed by a combination of: (i) potting or encapsulating the electronic component in a cavity of the implant with little or no void space; and (ii) pulsed laser welding of a weld plate over the cavity that provides a hermetic seal and that minimizes the thermal degradation of the encapsulant. Such a method may include: providing an implant and weld plate configured to provide offset weld lines around the periphery of the recess; injecting encapsulant at a first temperature and, prior to the welding of the weld plate to the device; exposing the cured encapsulant to an elevated second temperature; using pulsed laser welding parameters selected from the group consisting of: a pulse energy of in the range of from about 1 to about 3 J, a pulse duration in the range of from about 2 to about 8 msec, a pulse repetition in the range of from about 2 to about 8 Hz, a traverse speed in the range of from about 50 to about 150 mm/min, shield gas delivered at a rate ranging from about 10 to about 30 l/min at a pressure ranging from about 2 to about 4 bar, weld spot overlap ranging from about 35 to about 80%, weld penetration ranging from about 30 to about 85% and combinations thereof.

In a refinement, the welding parameters may be controlled to produce a desired overlap of the weld spots that can range from about 35 to about 80%, more preferably from about 70 to about 80%, while maintaining the temperature inside the cavity below about 150° C. to avoid thermal damage to the encapsulant.

In another refinement, the welding parameters may be controlled to produce a desired weld penetration that can range from about 30% to about 85%, more preferably from about 35% to about 50%, while maintaining the temperature inside the cavity below about 150° C. One specific, but non-limiting example, utilizes a pulse energy of about 2 J, a pulse duration of about 5 msec, a pulse repetition of about 5 Hz, a traverse speed of about 100 mm/min, argon shield gas delivered at a rate of about 20 l/min at 3 bar, weld overlap of greater than 50% and weld penetration of greater than 35%, while maintaining the temperature of the cavity below 150° C. Obviously, these parameters will vary depending upon the size, structure and materials of construction of the implant or device that will accommodate the electronic component(s) as well as the particular encapsulant used and the particular electronic component(s) that is being hermetically sealed in the implant.

In a refinement, the encapsulant is applied with a needle and pressurized syringe.

In another refinement, the encapsulant is also injected into the cavity of the implant that houses the electronic device or sensor using a sealed mold. In such a refinement, the silicone may be cured in the mold.

In a refinement, an implantable medical device is manufactured according to the disclosed methods. In a further refinement, improved IM nails are manufactured according to the disclosed methods.

The offset weld lines help minimize the amount of heat dissipated into the encapsulant during the welding step. A suitable offset for the weld lines ranges from about 250 to about 750 microns from the peripheral edges of the cavity. In one specific, but non-limiting example, the offset is about 500 microns. Obviously, this parameter will vary greatly, depending upon the particular implant.

Heat sinks can be located in the inner bore of the device and/or as an external sleeve with aperture to limit the heat transferred from the weld location to the encapsulant. The heat sinks can made from thermal conductors such as copper, silver or aluminum alloys.

To combine the advantages of aluminum and copper, heat sinks can be made of aluminum and copper bonded together. Thermally conductive grease may be used to ensure optimal thermal contact. If utilized, the thermally conductive grease may contain ceramic materials such as beryllium oxide and/or aluminum nitride, but may also or alternatively contain finely divided metal particles, e.g. colloidal silver. The heat sinks may be designed to have a substantial surface area with optional fins. In a refinement, a clamping mechanism, screws, or thermal adhesive may be used to hold the heat sink tightly onto the component to maximize thermal conductivity, without crushing or damaging the implant or electronic component. The heat sink can be modular in design enabling different size implants in terms of length and/or diameter to be fitted during the welding operation.

Silicone encapsulants may be typically cured at about 80° C. for a time period ranging from about 1 to about 2 hours or according to the manufacturer specifications. Post-curing of the encapsulant at an elevated temperature will enhance the physical and performance properties of the silicone by increasing cross-link density, mitigating out-gassing, removing volatile agents by diffusion and evaporation and allowing the material to become conditioned to the service temperature of the welding operation.

Following a normal cure cycle for a silicone, the silicone can be exposed to mild heat (from about 160 to about 180° C.) for a time period ranging from about 4 to about 8 hours. Lower temperature ranges can be used in a range of from about 100 to about 120° C. over longer periods (~24 hours). Insufficient curing can result in bubbling and production of potentially toxic monomers. On the other hand, increasing the temperature above 180° C. has been shown to have an adverse effect on the encapsulated electronic components.

The disclosed methods are useful for devices in which electronic components may be in close proximity with the parts to be welded and require a sealed environment. For example, the disclosed methods are useful in fabricating orthopedic, dental and maxillofacial devices and implants as well as a host of other non-medical applications.

The disclosed low-temperature pulsed laser welding methods are compatible with many soft elastomers in combination with an electronics module. In a refinement, the encapsulant is a soft elastomer. In another refinement, particularly for the fabrication of medical implants, the encapsulant may be a medical grade silicone. In other refinements, conformable potting materials, such as a bio-inert polymer, e.g. polyurethane, epoxy resin, and polyetheretherketone (PEEK) can be used as an encapsulant material.

The encapsulant may be used in combination with a biocompatible primer to promote adhesion to the implant base metal minimizing void formation within the cavity.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiments illustrated in greater detail in the accompanying drawings, wherein:

FIGS. 13A-13E illustrate a mold for injecting additional silicone into the implant to form that shape of the weld plate wherein FIGS. 13A and 13B are end views of molds for use with a curved weld plate (FIG. 13A) and flat weld plate (FIG. 13B), FIGS. 13C and 13D are plan views of the two mold halves of FIG. 13A and FIG. 13E is a top plan view of the mold half illustrated in FIG. 13C.

FIGS. 17A-17B are plan and side views illustrating the coupling of the copper heat sinks to an IM nail and wherein FIG. 17A illustrates the location of the spot welds of the weld plate to the disclosed IM nail.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

Figure 1A:
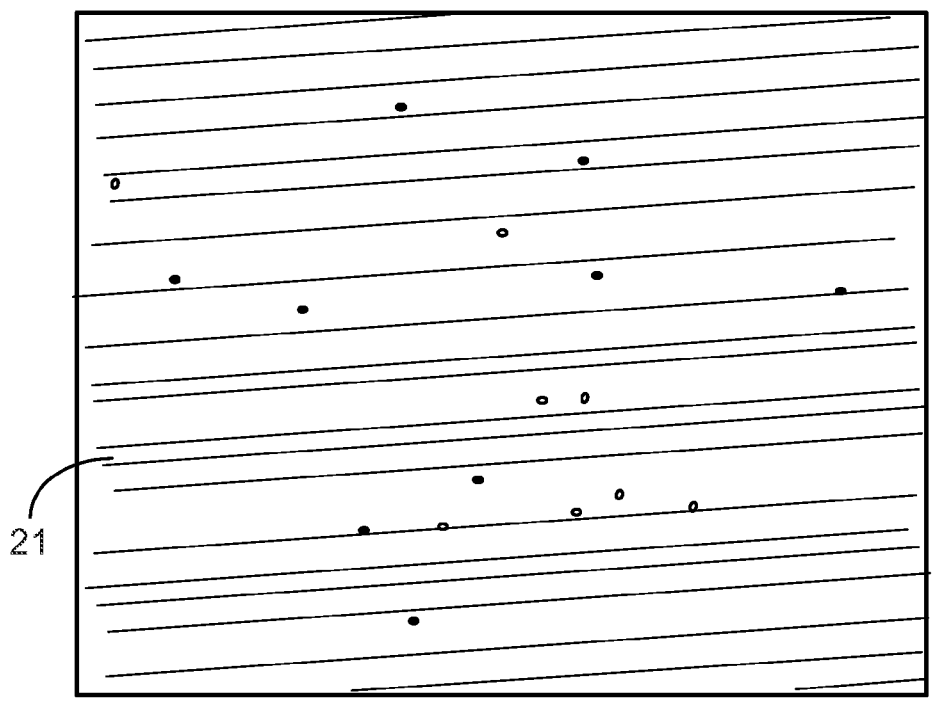
FIGS. 1A-1E illustrate cured MED3-4213 encapsulated in an implant (FIG. 1A) in the pre-welding condition (FIG. 1A) and after conventional welding (FIGS. 1B-1E).
Figure 1B:
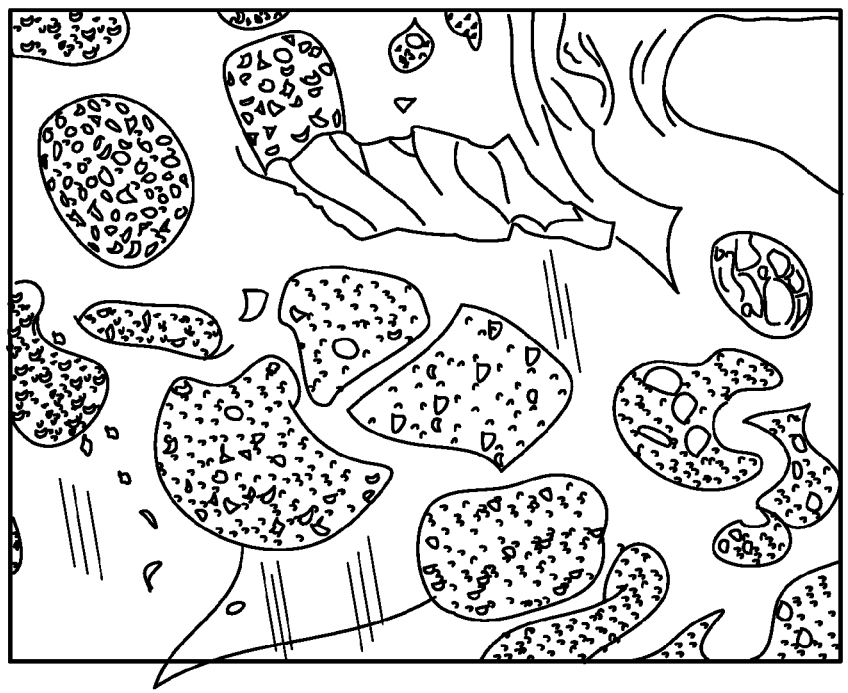
Figure 1C:
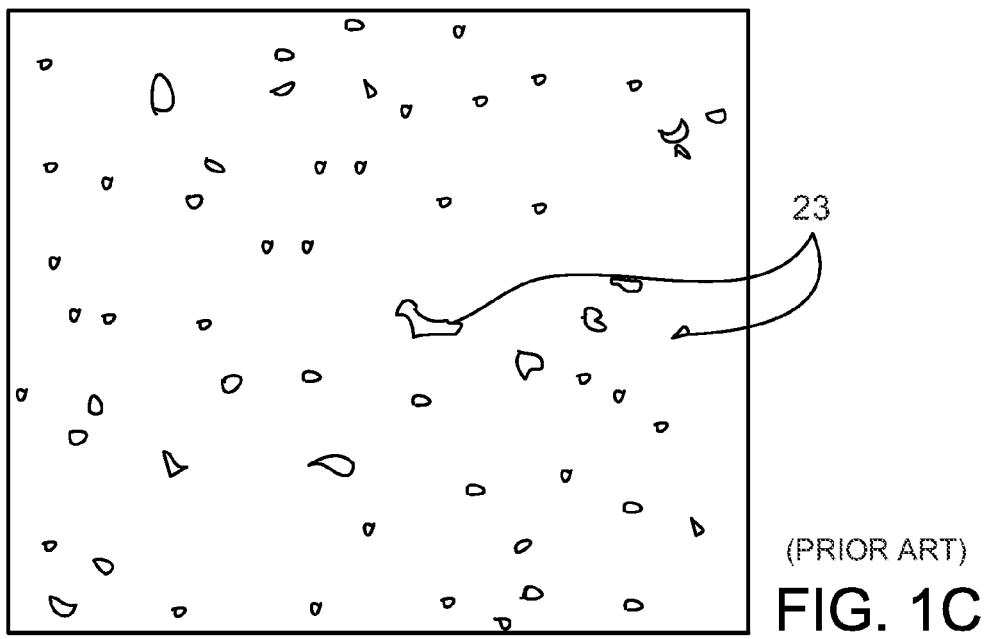
Figure 1D:
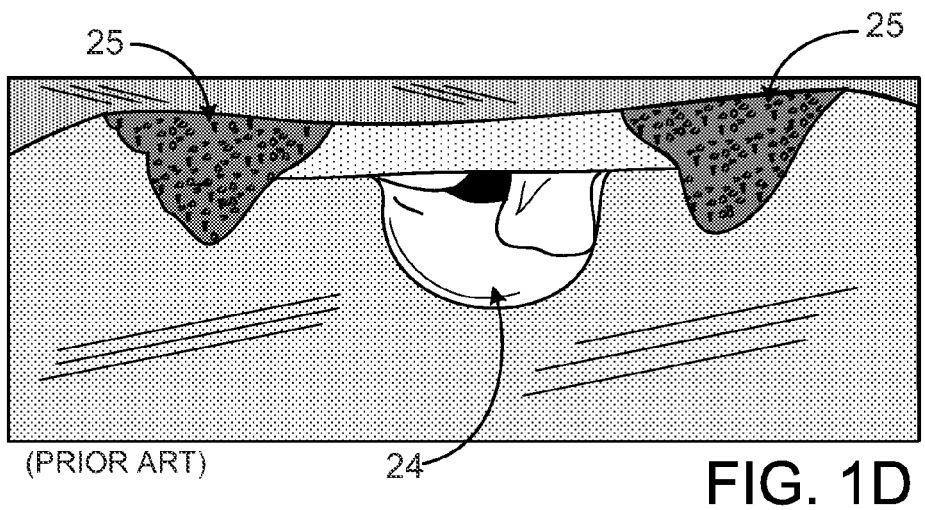
Figure 1E:
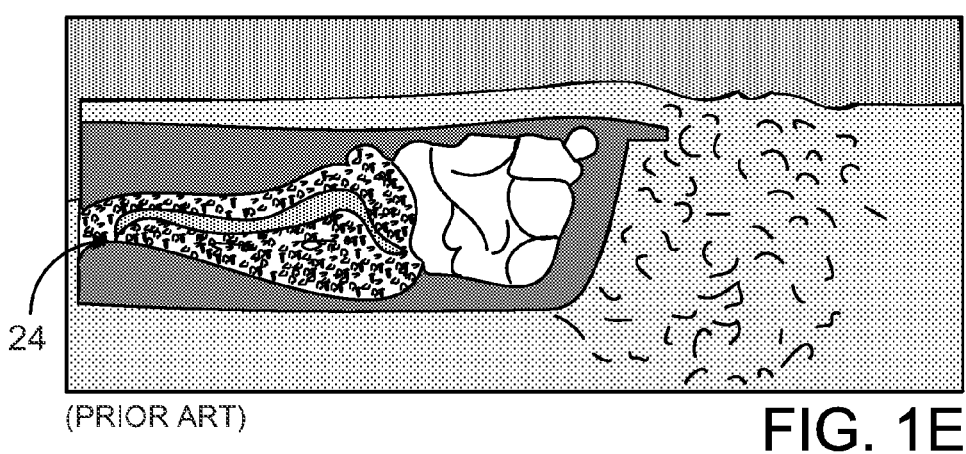
Figure 2:
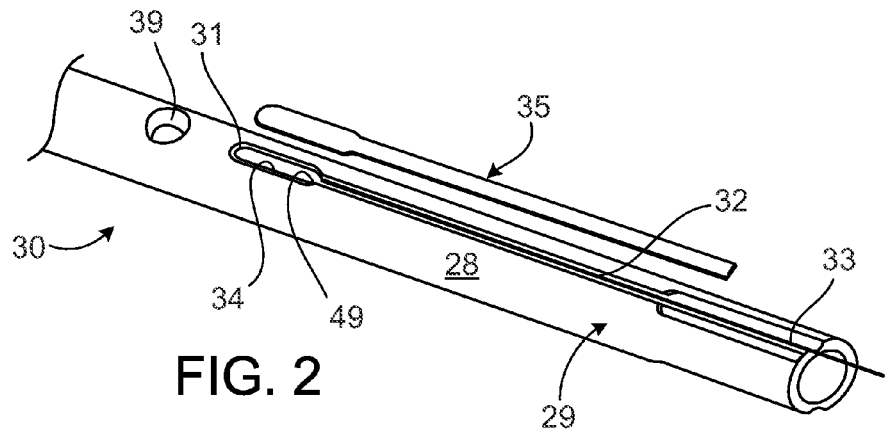
FIG. 2 is an exploded perspective view of a disclosed test implant illustrating a lead wire channel, a sensor cavity and a weld plate.

As an example, the fabrication of an IM nail 30 with an electronic component 31 and wire bus 33 is shown and described. Turning to FIG. 2, the IM nail 30 comprises a load-bearing structure in the form of a metallic (e.g., titanium) tube 29 with an outer surface 28. The outer surface 28 includes a long narrow channel 32 having a width or diameter of about 1 mm or less in the disclosed example and which may be used to house a multi-stranded wire bus 33. The wire bus 33 may extend outside of the structure of the nail 30 as shown in FIG. 2. The sensor 31 may also be designed for wireless communication and battery power thereby eliminating the need for the channel 32 and wire bus 33.

Figure 4:
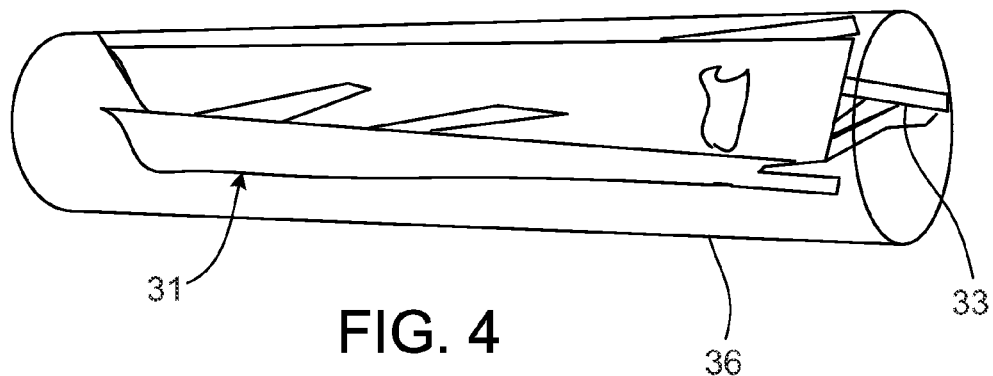
FIG. 4 is a perspective view of a sensor for use in a disclosed IM nail implant.

The outer surface 28 of the load bearing structure 29 also includes a larger cavity 34 for accommodating the sensor 31, which is also shown in FIG. 4. The weld plate 35 may be designed so weld lines (not shown in FIG. 2) surrounding the cavity 34 and channel 32 may be offset to ensure that the heat dissipated to the encapsulant during the welding step may be minimized. In one exemplary embodiment, an offset of about 500 microns was shown to be effective for a typical IM nail 30 subjected to a disclosed pulsed laser welding process. As described below, the encapsulant may be used to hold the sensor 31 in a fixed position within the cavity 34 for accurately indicating a position of a landmark, such as a screw hole 39 during installation of the nail 30 in a patient. The encapsulant may also be used to prevent body fluids from reaching the sensor 31 after implantation. This function is particularly important for sensors 31 having wire connections 33.

Figure 3A:
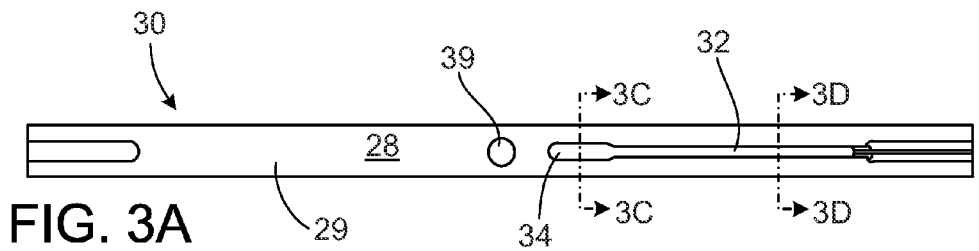
FIG. 3A is a plan view of a disclosed implant.
Figure 3B:
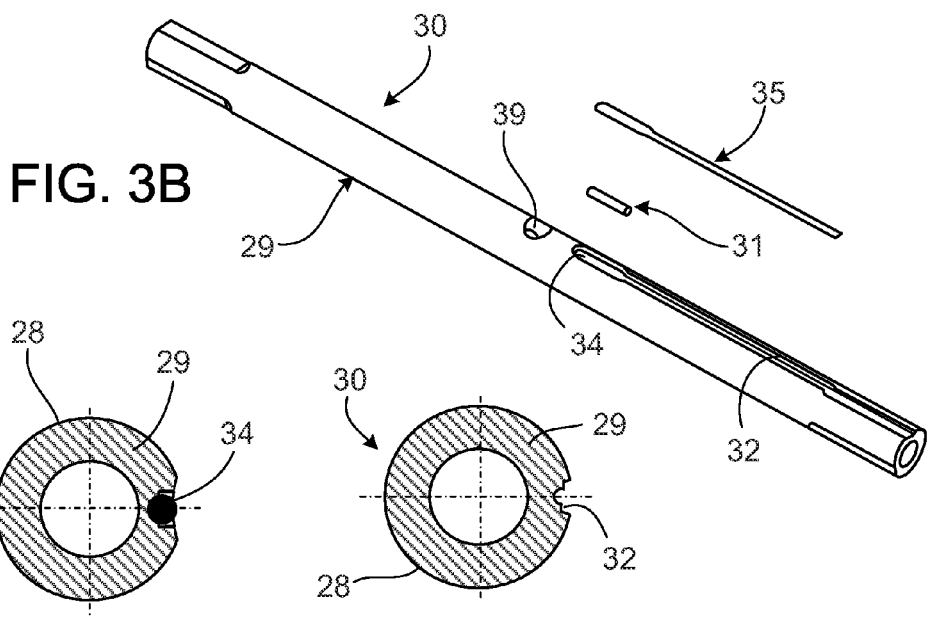
FIG. 3B is an exploded/perspective view of a disclosed implant, sensor and weld plate
Figure 3C:
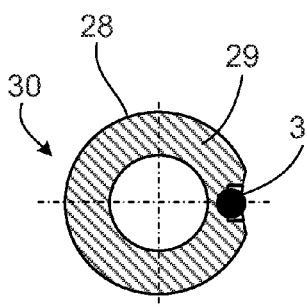
FIGS. 3C and 3D are sectional views taken substantially along lines 3C-3C and 3D-3D of FIG. 3A respectively.
Figure 3D:
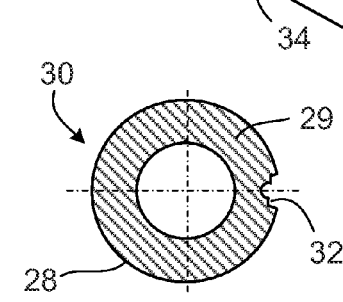
Figure 5A:
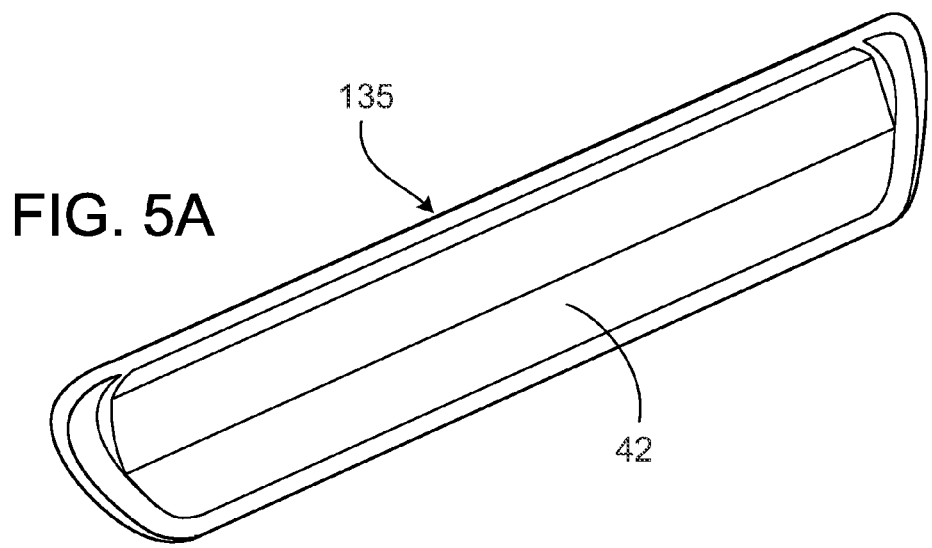
FIGS. 5A and 5B are perspective and end views respectively of a disclosed weld plate and FIG. 5C is a partial perspective and sectional view of a disclosed IM nail with a sensor disposed in the cavity of the IM nail beneath the weld plate of FIGS. 5A and 5B.
Figure 5B:
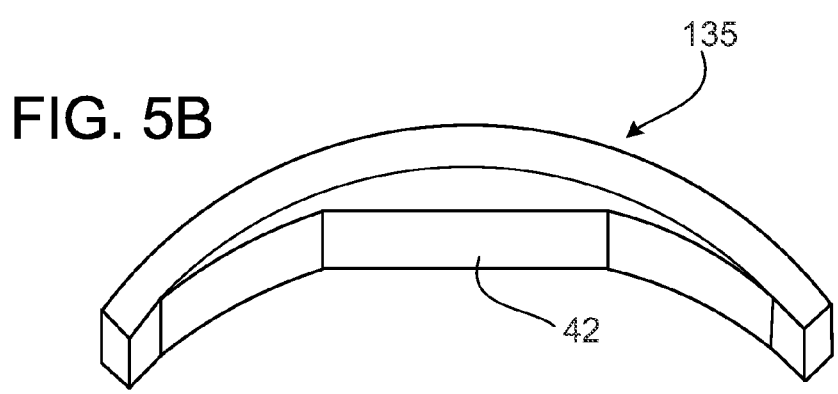
Figure 5C:
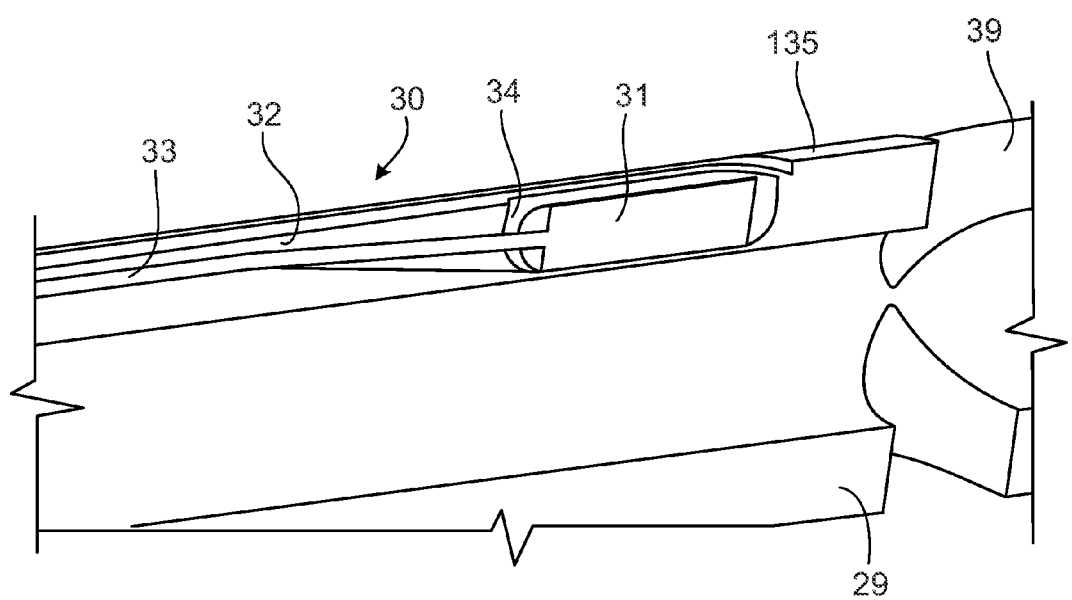

A plan view of the IM nail 30 is illustrated in FIG. 3A without the sensor 31 or wire bus 33. FIG. 3B is an exploded view of the IM nail 30, sensor 31 and weld plate 35. The sectional views of FIGS. 3C and 3D illustrate the relative sizes of the sensor cavity 34 and wire channel 32 respectively. A curved weld plate 135 that is compatible with different implant geometry is illustrated in FIGS. 5A-5C.

Preparation of the Encapsulant

Suitable silicone encapsulants for the disclosed implants include, but are not limited to, MED3-4213 and related products, from NuSil Silicone Technology with an onset thermal degradation temperature of about 230° C. A two-component silicone may be less convenient to use than one-component silicone because of the mixing requirement. However, in contrast to one-component silicones, two-component silicones require no atmospheric moisture for curing, and thus are necessary for closed mold applications such as the IM nails 30 disclosed herein. A mixer may be used to mix the two parts on exit from the dual-syringes.

Encapsulation or Potting of the Sensor Unit

A perspective view of a sensor 31 is illustrated in FIG. 4. In one example, the sensor 31 may be an electromagnetic tracking system to resolve the problem of a free-hand interlocking technique for locating distal screw holes 39 in an IM nail 30 as shown in FIG. 5C. Typically, such sensors 31 are provided with a protective sleeve or tube 36. To protect the sensor 31 from the ingress of fluid, potting the sensor 31 within the tube 36 is recommended.

The potting or encapsulation of the sensor 31 may be conducted without primer. The polyimide tube or sleeve 36 that will accommodate the sensor 31 may be inserted into a mold, such as a PTFE mold (not shown), ensuring the exposed end is level with the top of the mold. Then, silicone may then injected into the tube 36 starting with a needle at the bottom of the tube 36, allowing the tube 36 to be filled before slowly retracting the needle ensuring there is more silicone being injected into the void created by the retracting needle to ensure the needle does not draw in any air.

The sensor 31 may then be dipped into a separate supply of mixed silicone, slowly wetting the surface particularly between the coil and circuit board thus removing air bubbles. The wetting procedure may be done under a stereo microscope with a pair of fine curved tweezers. The sensor 31 may then be slowly inserted into the previously filled tube 36 held in the PTFE mold leaving the tube 36 filled and flush with the top of the mold.

If utilized, a second sensor (not shown) may then be coated with silicone as the first and placed next to the first sensor 31 back to back in the mold avoiding air trapped in-between the first sensor 31 and the second sensor (not shown) or between the either sensor and the mold. For IM nails 30 requiring four sensors, the mold may be placed in a pressurized chamber at about 1 bar (gauge) for about 20 minutes, and then removed from the chamber.

The mold and sensor 31 may then be cured at about 75° C. for about one hour. The mold may then be removed from the oven and allowed to cool before separating the mold parts and examining the encapsulated sensor 31 under the microscope.

Encapsulation of the Sensor and Wire Bus Using Pressurized Syringes

Figure 6:
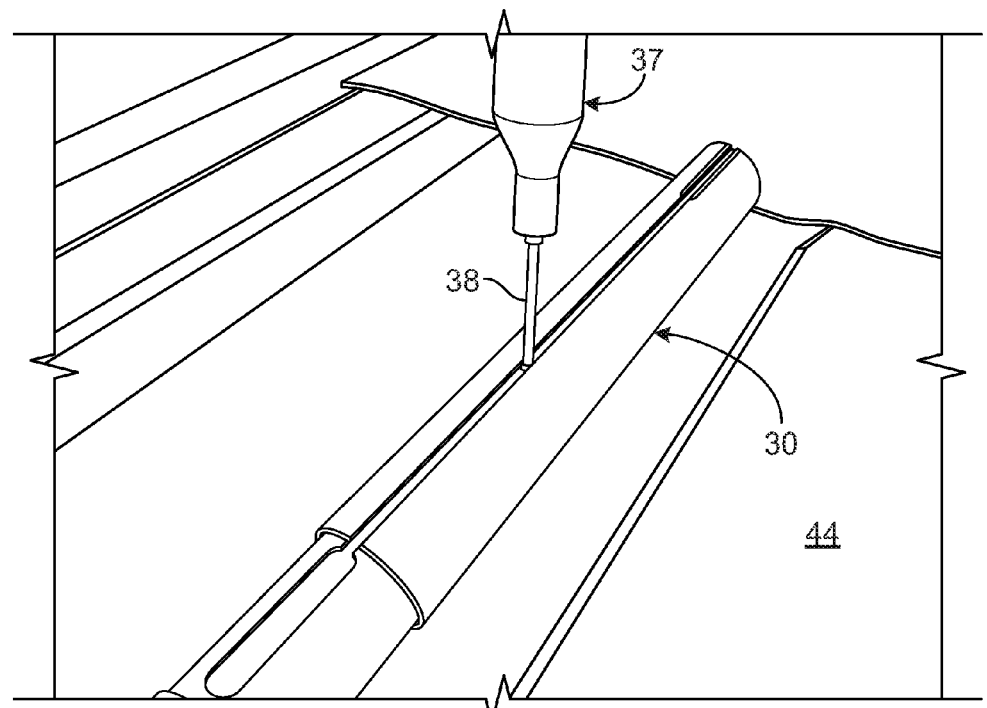
FIG. 6 illustrates the use of excess silicone within the channel of the IM nail that accommodates the wiring connected to the electronic component or sensor.
Figure 7:
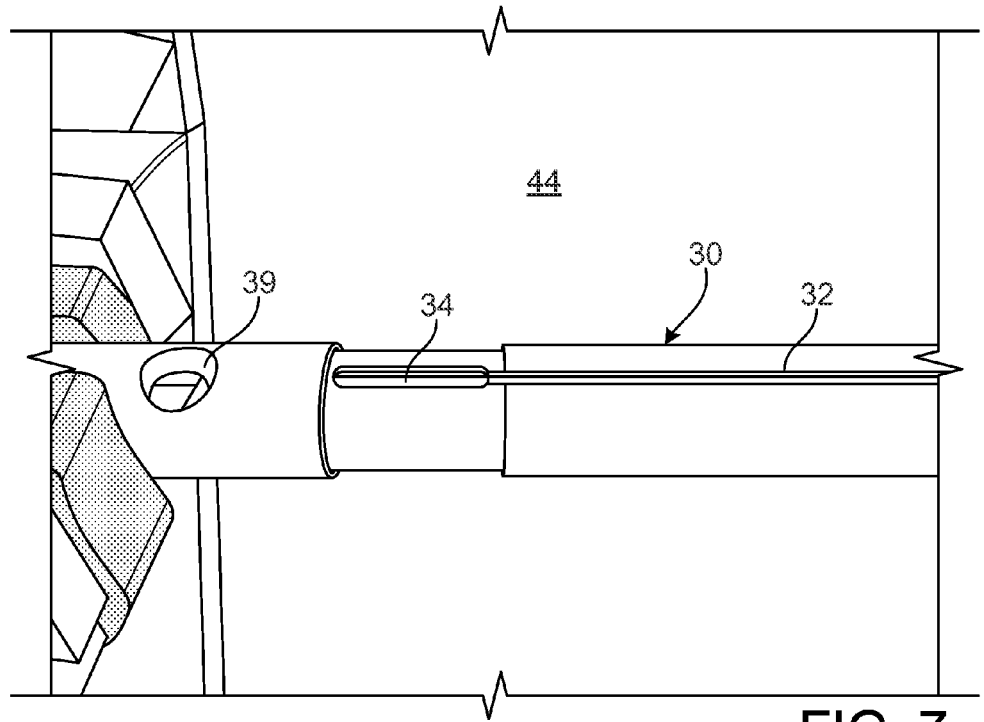
FIG. 7 illustrates the use of excess silicone within the sensor cavity.

Turning to FIGS. 6-7, the silicone may be applied using a syringe 37 and bore needle 38, such as a 0.65 mm bore needle 38, although the needle size may vary. Adhesion to the IM nail 30 may be greatly improved using a biocompatible primer, such as MED6-161 (NuSil Silicone Technology). Other biocompatible primers are available and known to those skilled in the art.

The sensor 31 and wire bus 33 encapsulation may be carried out using a pressurized syringe 37. The IM nail 30 is ultrasonically cleaned in propan-2-ol or any suitable degreasing solvent, as will be apparent to those skilled in the art. Any microscopic burrs or swarfs are preferably removed from the channel 32 and cavity 34 as they could damage the insulation on the wire bus 33. The IM nail 30 may then be wiped clean with acetone or another suitable solvent. An ultrasonic cleaning device may be employed. Lint-free tissue may be used and has been found to be adequate. The wire bus 33 is placed flat on a surface in a straight configuration to ensure that the wire lies straight or axially at the bottom of the channel 32. Some space between the channel 32 and sensor cavity 34 may prevent the wire bus 33 from snagging and shorting against the IM nail 30 body. A temporary domed end plug 41 (FIG. 10A) with groove (not shown) is inserted into the end of the IM nail 30. This permits the wire bus 33 to be looped over the end of the IM nail 30 and across to the other side of the IM nail 30 and held with a little tension without causing sharp bends. The domed end plug 41 helps curve the wire bus 33 smoothly. Tape may be used to anchor the wire onto the IM nail 30.

A primer, such as MED6-161 (NuSil Silicone Technology—www.nusil.com), or other suitable material, is coated inside the channel 32, sensor cavity 34, and on the sensor 31. Because MED6-161 is viscous, only a microscopic amount may be needed at the bottom of the channel 32 where surface tension diffuses the primer across the channel 32. One drop using a 1 ml syringe with a MICROLANCE™ No. 18 (0.5×25 mm) syringe with squared off point was used in one successful procedure.

The syringe 38 may be dragged along the length of the channel 32 to wet the inside surface. Preferably, the primer is not allowed to run over the edge of the channel 32. If it does, a re-clean and restart is recommended. The sensor 31 may be primed easily by dipping it and wiping excess of with a lint-free tissue. All this was done under a stereo microscope with ×20 magnification. Dry time is about 30 minutes. An anti-adhesive pure soap solution is applied to adjacent external surfaces inclusive of flat recess where the weld plate 35, 135 is welded.

The silicone can be very difficult to remove or even see, and therefore an anti-adhesive surface coating may be used to coat all external surfaces where silicone coating is not required. One useful coating is a 50/50 mixture of liquid soap and de-ionized water applied to the recess in the same way as the primer in the channel 32 using a similar needle and syringe, and the remaining surface with slightly dampened cotton bud. The IM nail 30 may then be allowed to air dry.

Silicone is then applied inside the channel 32. A hand-held dispenser may be prepared with a flattened 0.65 mm ID, 0.9 mm OD needle (or other suitable needle, depending on the structure being filled) and the silicone may be applied in the sensor cavity 34 under the same microscope with ×20 magnification. Enough silicone be applied to the internal surfaces with a little excess to half-fill the channel 32. Silicone may then be applied at a steady rate along the channel 32, using a numerical control (NC) machine table 44 (FIGS. 6-7), at a speed ranging from about 1 to about 3 cm/min, more preferably about 2 cm/min and a force ranging from about 90 to about 270 N, more preferably about 180 N on the dispenser so the silicone overfills the channel 32.

Figure 8:
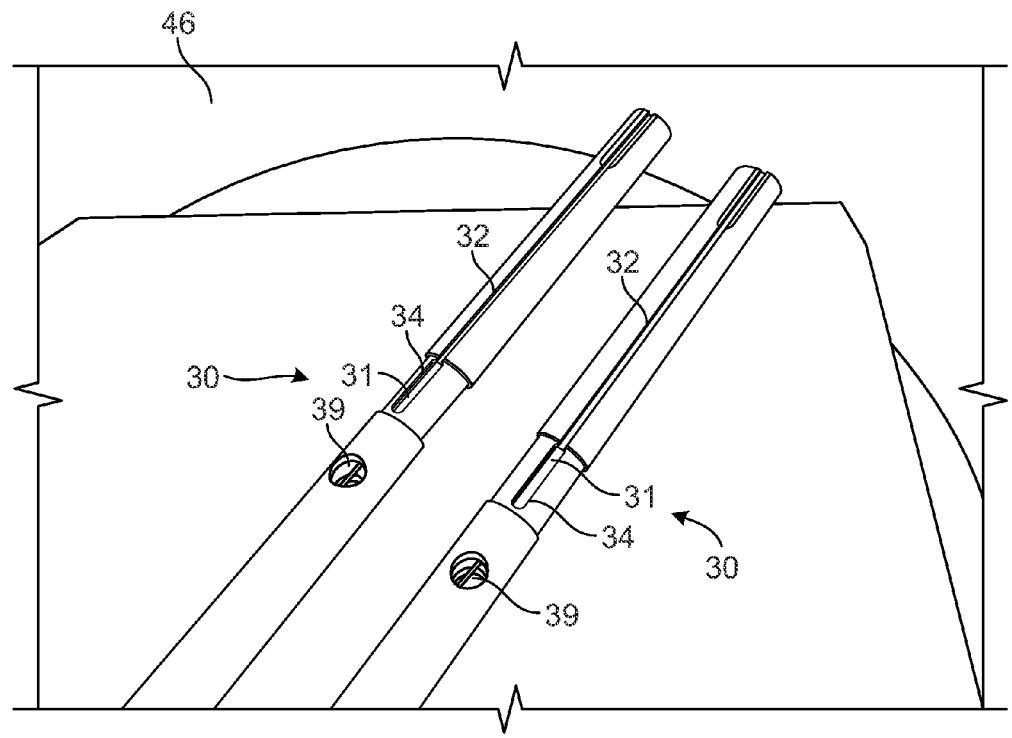
FIG. 8 illustrates silicone-coated implants placed in a pressure chamber for removing bubbles formed during the curing of the silicone.
Figure 9:
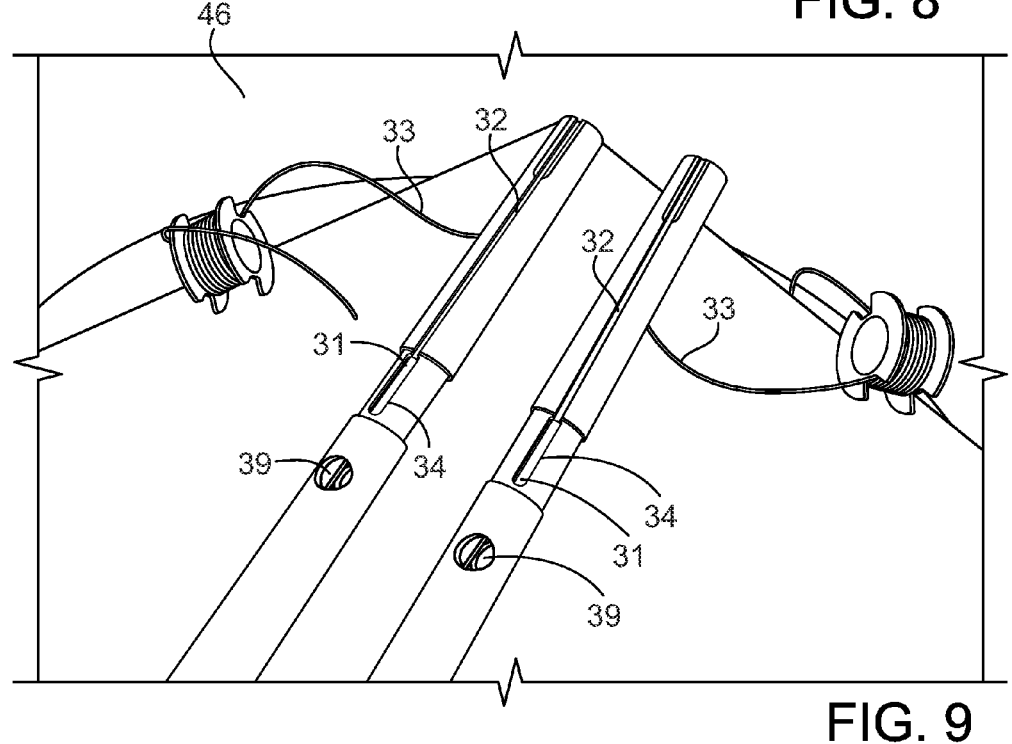
FIG. 9 illustrates a vacuum/pressure cycling within the pressure chamber used to remove air bubbles from the cured silicone.
Figure 10A:
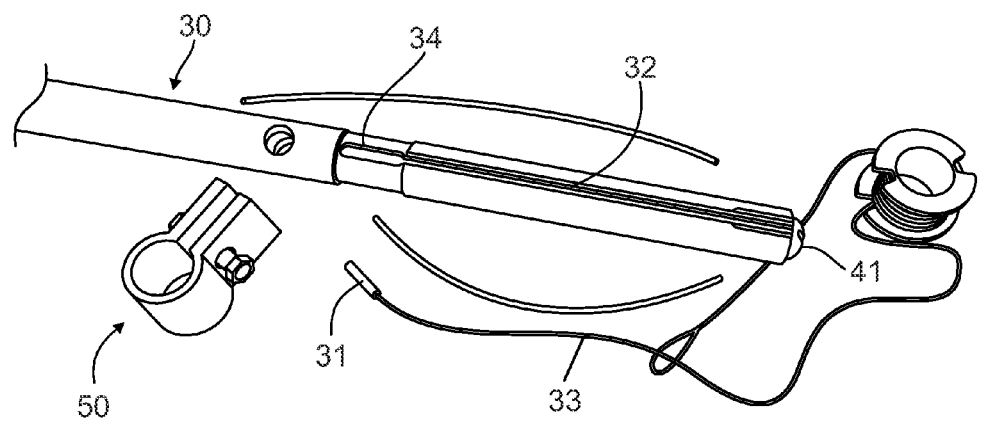
FIGS. 10A-10C illustrate a PTFE clamp, an IM nail and a wire bus (FIG. 10A), wherein the clamp is used to squeeze excess silicone out of the cavity prior to assembly (FIG. 10B), which placed over the sensor cavity with a wire notch in line with the wire channel, and which is tightened with a screw thereby squeezing excess silicone to the sides of the cavity (FIG. 10C).

The silicone should be free of air bubbles to avoid any water vapor condensing at the interface with the electronics causing adverse effects such as current and corrosion. This can be achieved by holding the point of the needle 38 against the bottom of the channel 32 while traversing along the channel 32. The IM nails 30 may then placed in a chamber 46 as shown in FIGS. 8-9 and the chamber 46 is then pressurized. The coated IM nails 30 are placed in the pressure chamber 46 for a time period ranging from about 20 to about 30 minutes as shown in FIG. 8. After pressurization, any bubbles that are raised to the surface may be removed. It is advantageous to remove as many bubbles as possible or avoid bubbles altogether. The sensor 31 may then be placed at an angle and gently lowered into position in the recess with the wire bus 33 that is lowered into position in the channel as shown in FIGS. 9 and 10A. Avoiding the use of implements to push the wire bus 33 may avoid the creation of bubbles. Slight tension in the wire bus 33 may be used to gradually lower the wire bus 33 into the silicone and the channel 32. The wire bus 33 does not need to reach the bottom of the channel 32.

Figure 10B:
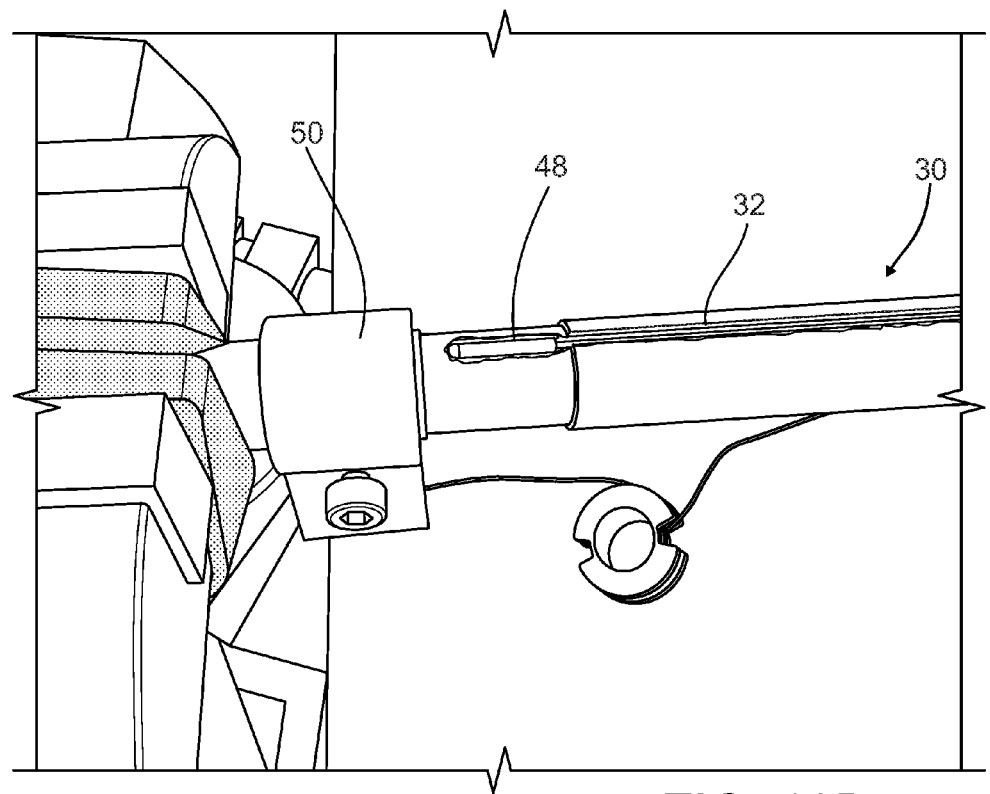
Figure 10C:
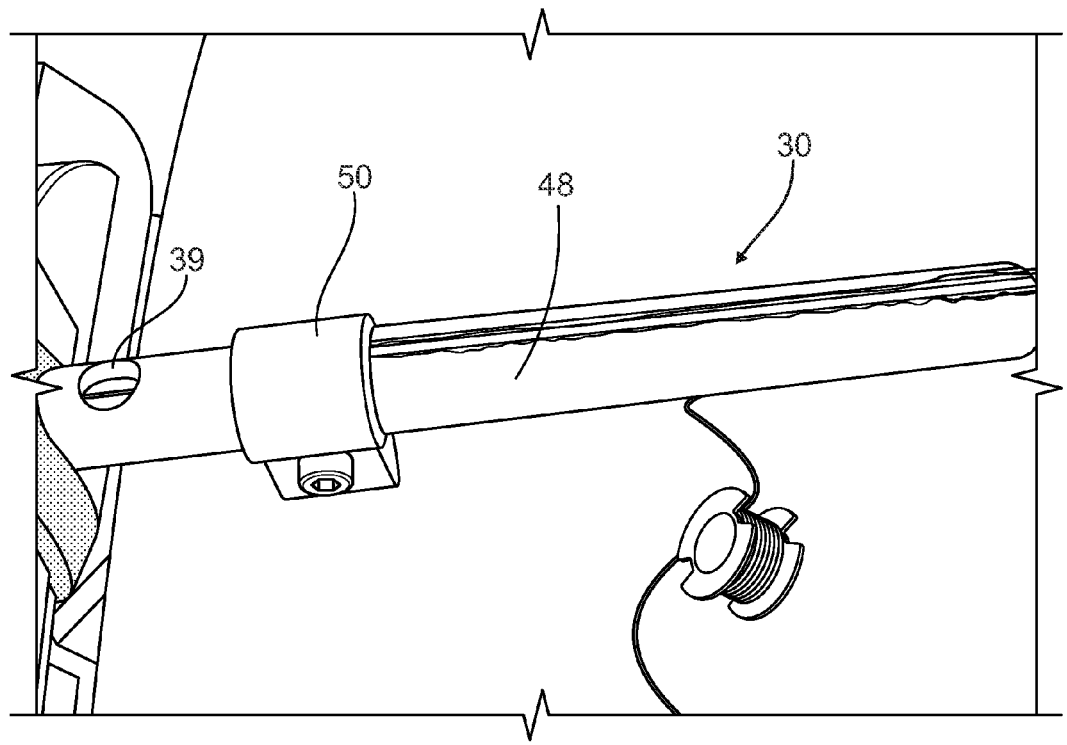

When the sensor 31 is in place in the cavity 34, tape 48 and tension to the wire bus 33 is applied at the end of the IM nail 30 as shown in FIGS. 10B-10C. By applying tension to the wire bus 33, the sensor 31 move against the cavity shoulder 49 (FIG. 2) and the wire bus 33 moves further down into the silicone as it straightens. The wire bus 33 may then be looped over the end plug 41 (FIG. 10A) and taped on the opposite side under tension as shown in FIG. 10C.

Vacuum/pressure cycling is performed in the chamber 46 shown in FIG. 9. One suitable pressure cycle is as follows: vacuum ranging from about −0.4 to about −1.2 bar (gauge), preferably about −0.8 bar (gauge) for a time period ranging from about 1.5 to about 3.5 minutes, preferably about 2.5 minutes, followed by about 1.5-3.5 minutes at atmospheric pressure, preferably about 2.5 minutes. The cycle may be repeated as necessary before applying a constant pressure ranging from about 1 to about 3 bar (gauge), preferably about 2 bar (gauge) for about a time period ranging from about 10 to about 30 minutes, preferably about 20 minutes. The vacuum cycle causes air from the space between the wires 33 to be flushed out and the pressure then removes air bubbles from the silicone. Again, after pressurization, any bubbles that have risen to the surface are preferably removed.

The sensor 31 is then held in place using a PTFE clamp 50 (FIGS. 10A-10C) or a clamp made of another suitable material. With the silicone still workable and with the IM nail 30 held in one hand, a purpose-made flat-bottomed PTFE clamp 50 (FIG. 10B) is placed over the sensor cavity 34 with a protruding ridge in line with the wire channel 32 to mold the top surface of the silicone flush with weld plate 35, 135. Two types of clamps 50 may be used. One clamp 50 to flatten the surface above the sensor cavity 34 with an extended ridge of about 0.5 mm in height protruding into the long channel 32 in order to mold the first application of silicone with sensor 31 and wire bus 33 as deeply as possible. A second clamp (not shown) may be used to flatten the surface above the wire channel 32 during the second silicone application. To ensure the clamp 50 is sitting within the recess where the weld plate 35, 135 is to be welded, additional clamps (not shown) may be used to press excess silicone to the sides of the cavity 34 and channel 32.

Figure 11:
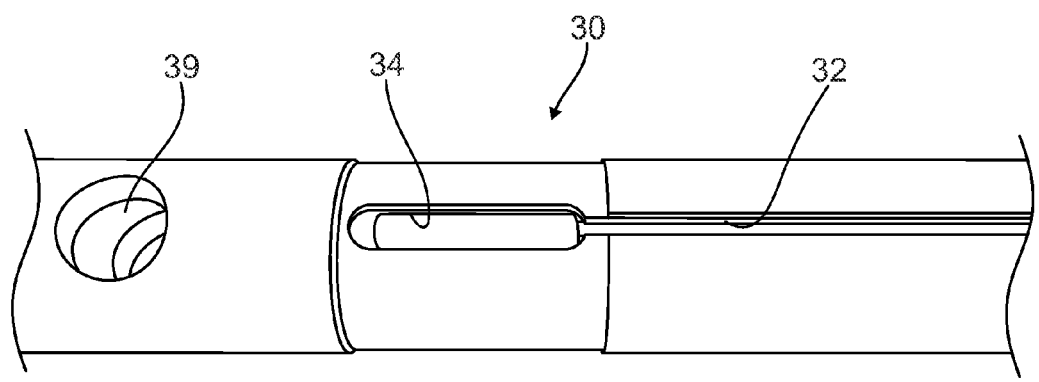
FIG. 11 illustrates the potted cavity after removal of PTFE clamp.

Air should not be permitted to enter between the PTFE clamp 50 and the sensor cavity 34. The IM nail 30 is cured for a time period ranging from about ½ hour to about 1.5 hours, preferably about 1 hour, at room temperature followed by about ½ to 1.5 hour cure, preferably about 1 hour at a temperature ranging from 30 to about 55° C., more preferably from about 40 to about 45° C. The PTFE clamp 50 is removed with the other PTFE parts from the outer surface as shown in FIG. 11. Then, any excess silicone may be removed. This may be done under a stereo microscope with ×20 magnification.

Figure 12A:
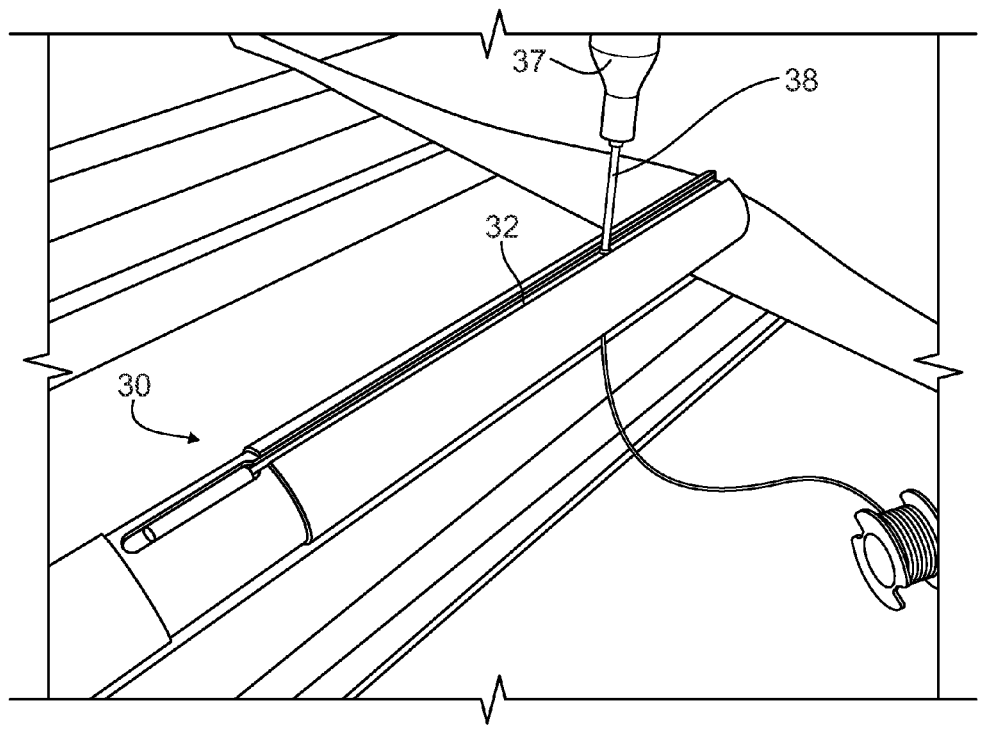
FIGS. 12A-12B illustrate the application of the second layer of silicone to the wire channel at a steady rate using a controlled, pressurized syringe, so the wire channel is slightly over-filled.
Figure 12B:
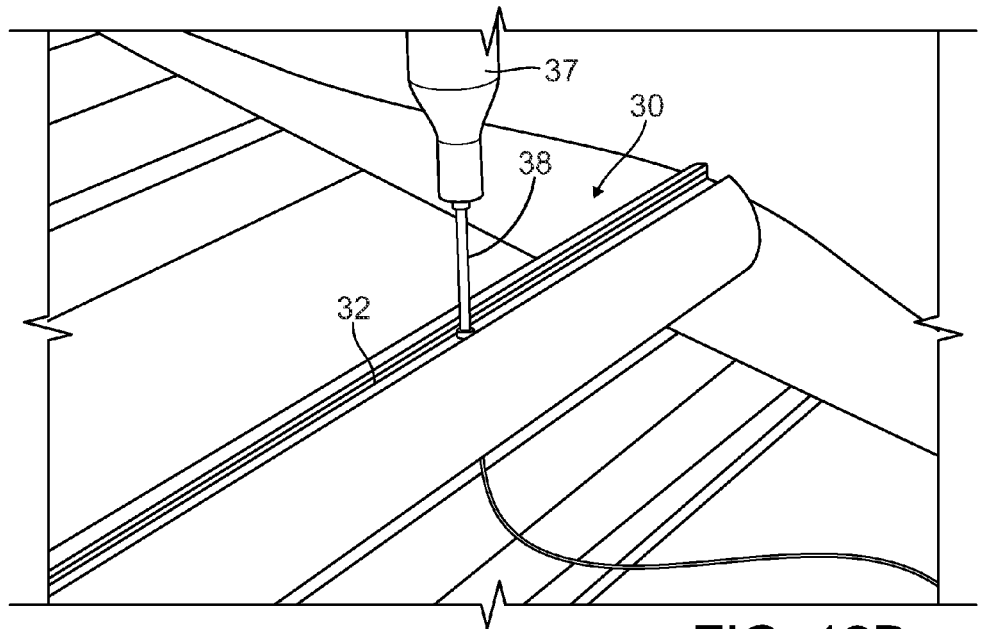

A second layer of silicone is then applied to channel as shown in FIGS. 12A and 12B. As before, silicone is applied into the long channel 32 at a steady rate using the needle 38 with a slight overfill. With the needle 38 used in the previous application positioned just inside the channel 32 and with a force ranging from about 25 to about 45 kg, for example, a 34 kg force, silicone may be deposited at a rate of 1 to 2 cm per minute. Again, air bubbles are to be avoided. A vacuum/pressure cycling may be performed in the chamber 46. The same pressure cycle as before may be used, for example: vacuum at about −0.8 bar (gauge) for about 2.5 minutes followed by about 2.5 minutes at ambient pressure. Obviously, these parameters can vary, as will be apparent to those skilled in the art. The cycle may be repeated twice and then a constant pressure at about 2 bar (gauge) may be applied for about 20 minutes. Again, after pressurization, any bubbles that have risen to the surface are preferably removed.

The IM nail 30 is cured for about 1 hour at room temperature followed by another hour at a temperature ranging from 40 to about 45° C. Again a modified curing cycle may be used: 1 hour at room temperature followed by 1 hour at 40-45° C. After cooling the PTFE clamps 50 may be removed. Any excess silicone may be removed as described above. The IM nail 30 is then cleaned and examined. The IM nail 30 may be carefully washed under running warm water and rinsed in de-ionized water before wiping using lint free cloth. The IM nail 30 may then be checked under a stereo microscope with ×20 magnification for any residue of silicone on the adjoining surfaces in particularly, the weld area.

Further Encapsulation of the Sensor and Wire Bus Using a Sealed Mold

Figure 13A:
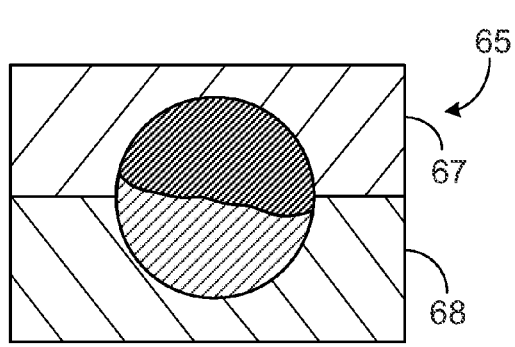
Figure 13B:
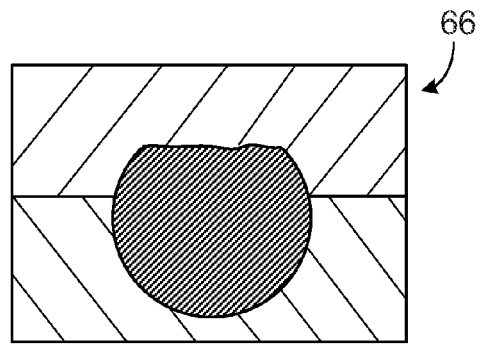
Figure 13C:
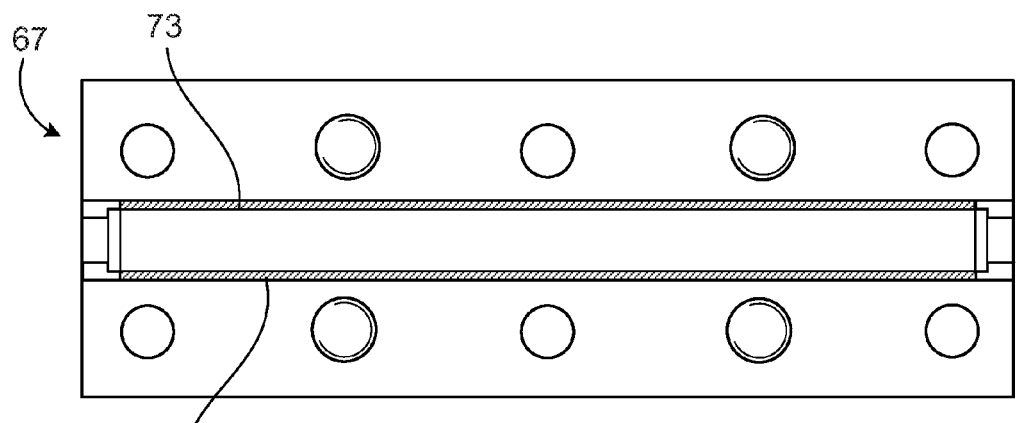
Figure 13D:
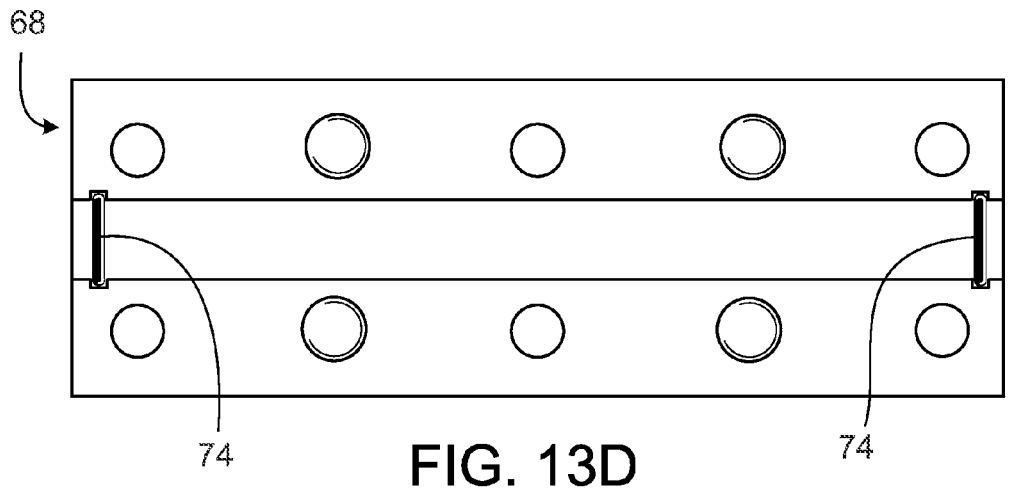
Figure 13E:
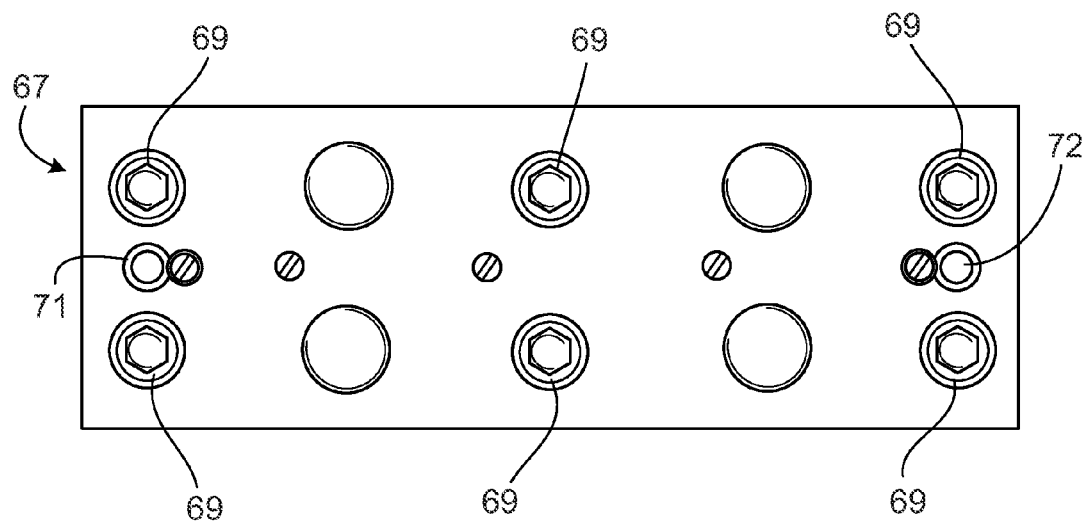

Turning to FIGS. 13A-13B, two molds 65, 66 are illustrated for providing an upper surface of the silicone encapsulant that matches the undersurface of the weld plate 35, 135. The mold 65 can be used with the curved weld plate 135 of FIGS. 5A-5C and the mold 66 can be used with the implant 30 and flat weld plate 35 of FIGS. 2-3D. The inner surfaces of the mold halves 67, 68 are illustrated in FIGS. 13C-13D. A top view of the mold half 67 is illustrated in FIG. 13E.

To prevent the silicone from sticking to the mold 65, a layer of HAEMOSOL™ or other release fluid may be applied to the mold 65. The IM nail 30 may be cleaned with iso-propyl alcohol or another suitable solvent. The mold 65 is heated to a temperature ranging from about 45 to about 70° C. prior to injection of the silicone. The mold 65 is the assembled around the nail 30 with the gaskets 73 and o-rings 74 providing a seal between the mold 65 and IM nail 30. The threaded bolts 69 are tightened and silicone is injected through inlet port 71 which is in alignment with the sensor cavity 34 until the silicone flows through the outlet 72. A NYLON™ screw is used to plug the outlet 72. Pressure is applied with the silicone injector for about 5 minutes. The injector nozzle (not shown) is removed and the inlet port 71 is plugged with a NYLON™ screw. The mold 65 is then placed in a pressure chamber (not shown) to ensure a regulated pressure is achieved during a long cure at room temperature. The mold is then placed in an oven at a temperature of about 70° C. and for about 3 hours.

Post-Curing Conditioning of the Encapsulant

Silicone encapsulants may be typically cured at about 80° C. for about 1 to about 2 hours, or according to the manufacturer instructions. Post-curing treatment of the silicone at an elevated temperature (160-180° C.) for about 24 hours will increase cross-link density, remove volatile agents and allow the material to become conditioned to the service temperature of the welding operation. Increasing the post-cure temperature above 180° C. may have an adverse effect on the encapsulated electronic components.

Instead of a complete encapsulation of the sensor 31 in the silicone, a suitable silicone plug can be created in the channel 32 or in the cavity 34 of the implant to adequately protect the sensor 31 from body fluids.

Hermetic Sealing of the Encapsulated Sensor and Wire Bus

Figure 14:
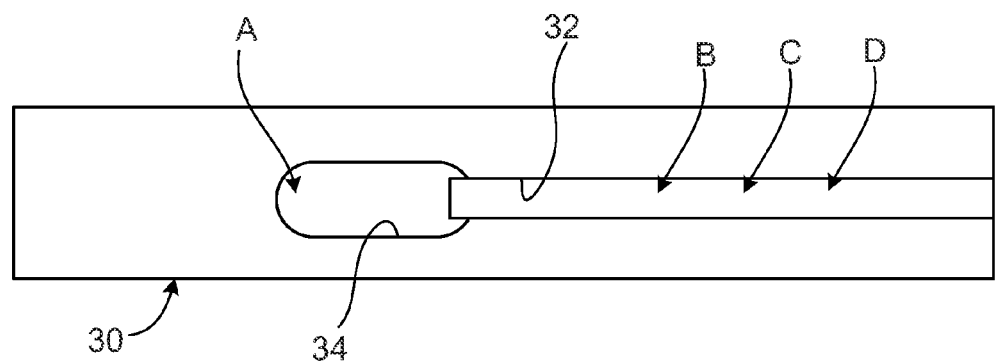
FIG. 14 is a schematic view of a disclosed IM nail implant illustrating the positions on the implant where the temperature was measured during the welding operation and reported in Table 1.

Temperature sensing experiments may be carried out to assess the in-line temperature during laser welding with and without the use of copper heat sinks. This is achieved using self adhesive indicators (temperature dots, RS products) which change color (i.e., blacken or darken) when the activation temperature is exceeded. The positions of the dots are illustrated schematically in FIG. 14. One dot (A) is located in the sensor cavity 34 and three dots (B, C & D) may be positioned along the main wire channel 32.

Temperature sensing data generated from three test IM nails 30 (HS1, HS2 and HS3) equipped with temperature sensing dots is summarized in Table 1. For sample HS1, the temperature at spots A and D exceeded 149° C. The pulse energy, pulse duration, pulse repetition rate and traverse speed were ~2 J, ~5 msec, ~10 Hz and ~100 mm/min respectively. The addition of copper heat sinks 55 (FIGS. 16A-16B), removal of the weld plate component and reduction in pulse repetition rate from 10 top 5 Hz with sample HS2 reduced the temperature at point D to below 150° C. (Table 1). With sample HS3, the weld plate component is added and the temperatures recorded at points A ("TA"), B ("TB"), C ("TC") and D ("TD") were TA<149° C., TB<210° C., TC<204° C. and TD=>149° C. respectively (Table 1). All other weld parameters may be held constant.

TABLE 1

| Sample ID | Laser welding conditions | Sensor location | Result |
|---|---|---|---|
| Sample HS1 | 2 J, 5 msec, 10 Hz, 100 mm/min° C., with weld plate, no heat sinks | 149° C. Temperature dots applied at A and D. | TA > 149° C.; TD > 149° C. |
| Sample HS2 | 2 J, 5 msec, 5 Hz, 100 mm/min° C., no weld plate, both heat sinks added | 149° C. Temperature dots applied at A and D. | TA < 149° C.; TD > 149° C. |
| Sample HS3 | 2 J, 5 msec, 5 Hz, 100 mm/min° C., with weld plate, both heat sinks added | Temperature dots applied: A = 149° C., B = 210° C., C = 204° C., D = 149° C. | TA < 149° C.; TB < 210° C.; TC < 204° C.; TD => 149° C. |

Figure 15A:
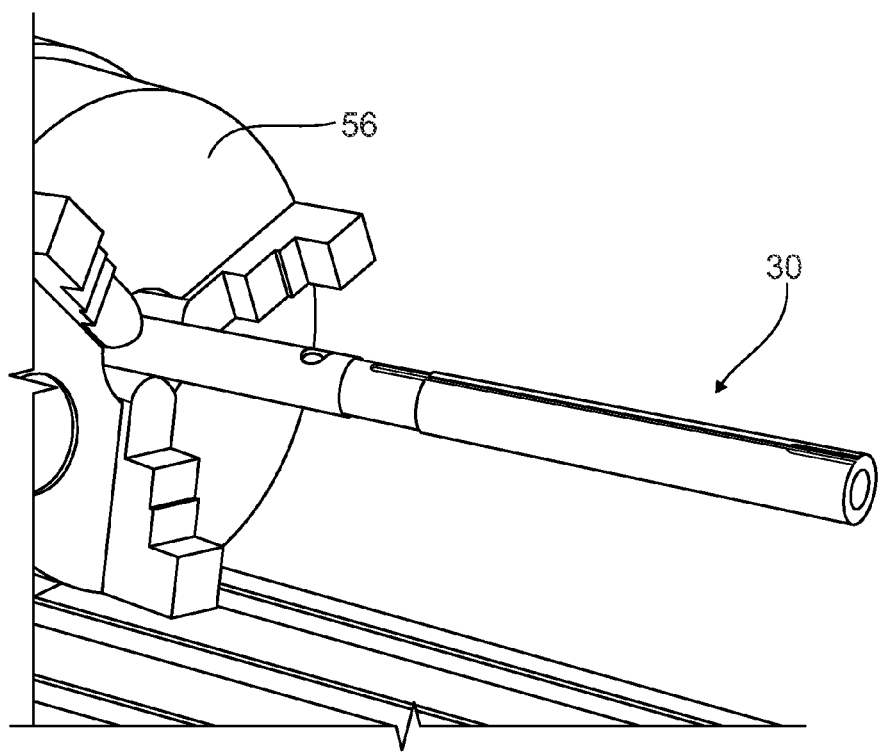
FIGS. 15A-15B respectively illustrate the mounting of a disclosed IM nail in a chuck of the rotary jig (FIG. 15A) and the attachment of three tacking clamps (FIG. 15B) with the shield gas nozzle in position.
Figure 15B:
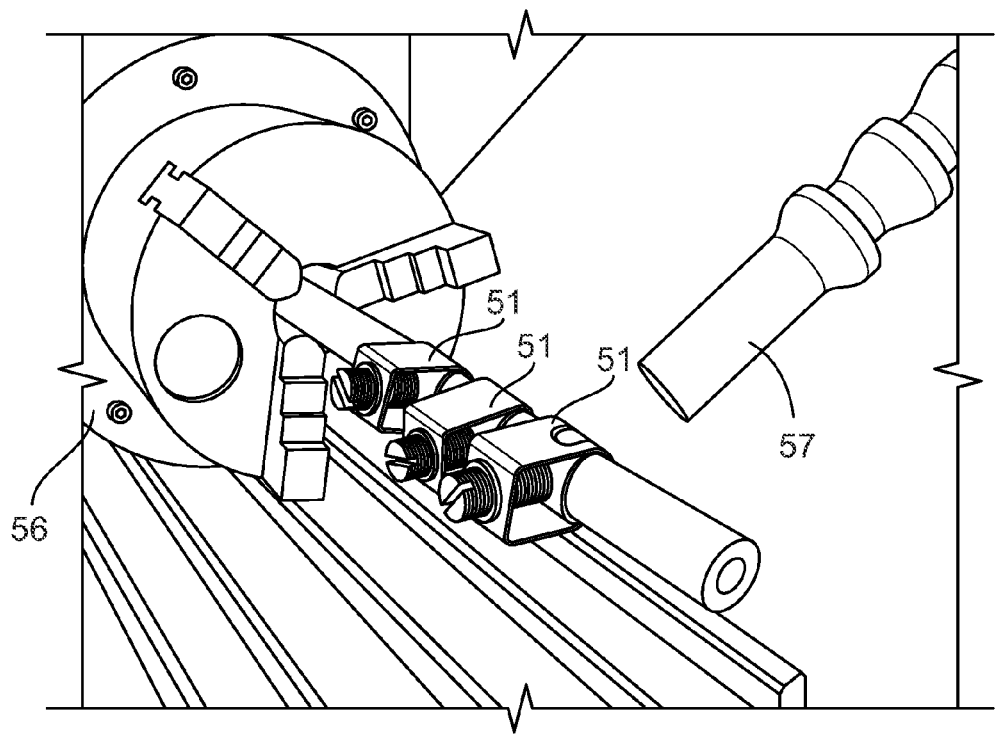
Figure 16A:
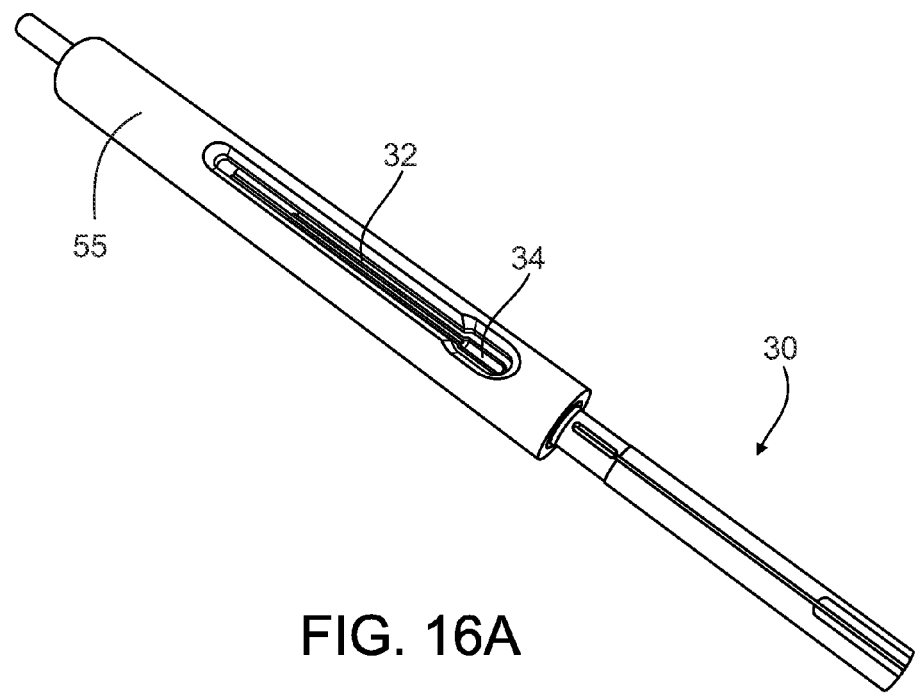
FIGS. 16A and 16B illustrate the outer heat sinks used to reduce the peak temperature during pulsed laser welding of the weld plate over the sensor cavity and wire bus channel.
Figure 16B:
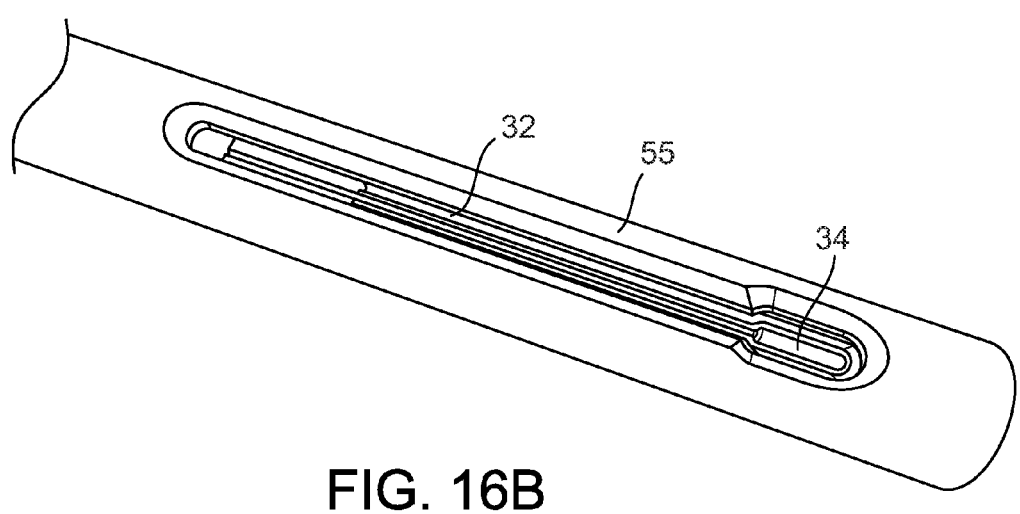
Figure 17B:
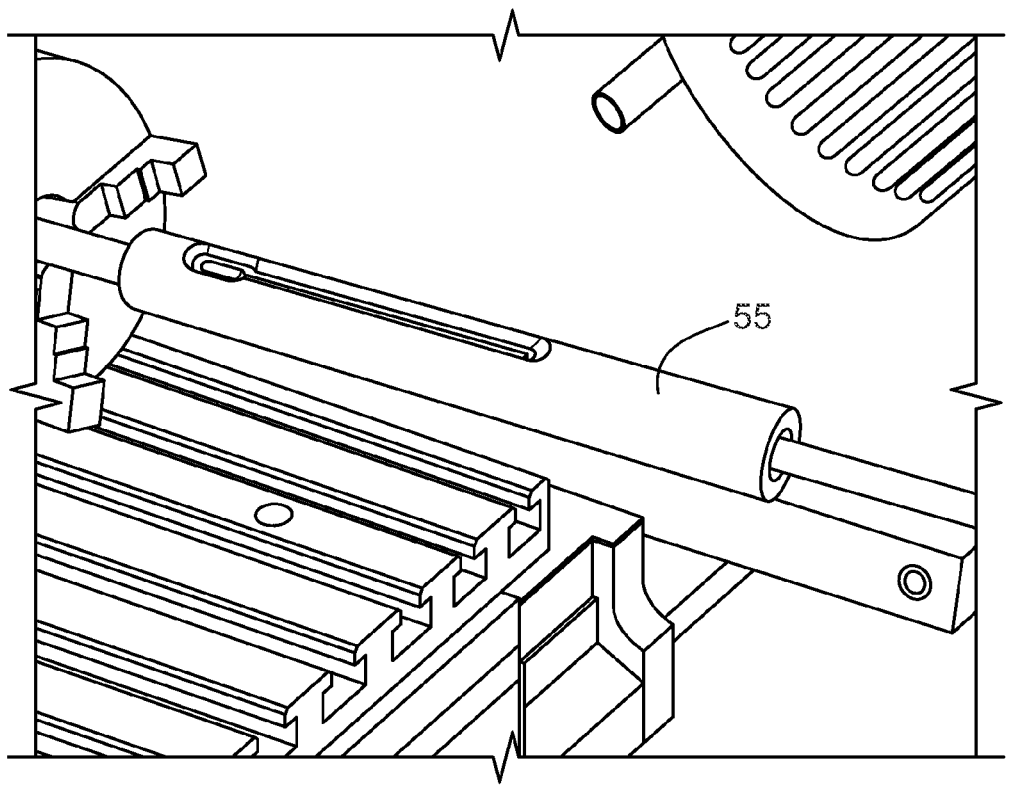
Figure 18:
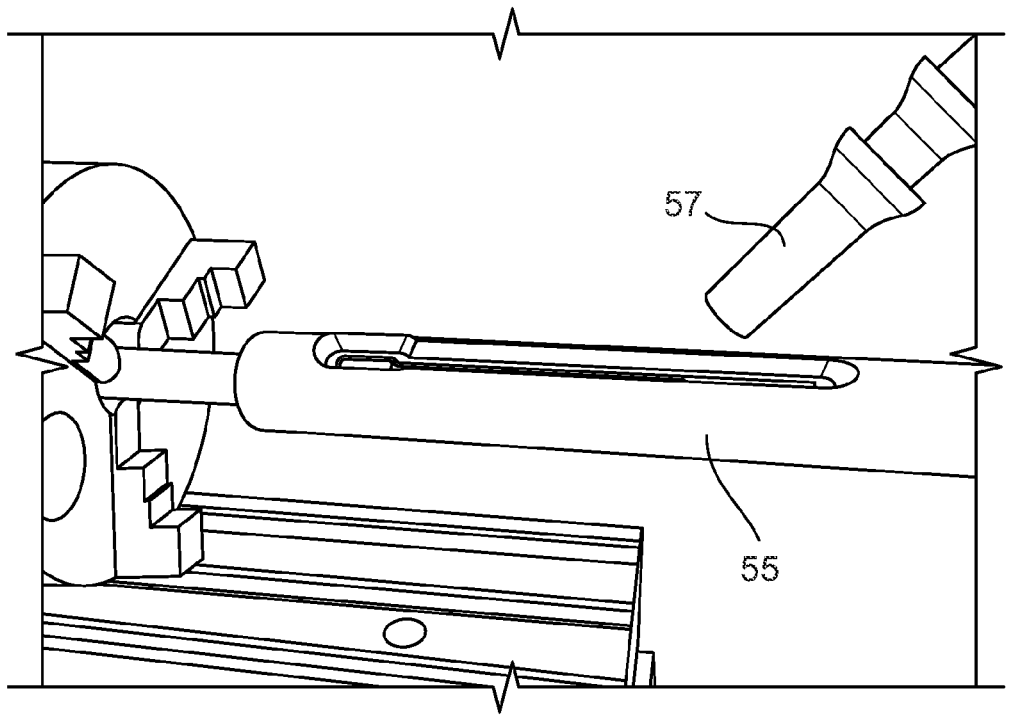
FIG. 18 illustrates the shield gas nozzle and heat sink disposed over an IM nail.

One exemplary procedure used to generate a low temperature weld procedure comprises: checking the IM nail and weld plate for a proper fit; mounting the IM nail in a rotary jig or chuck 56 (FIG. 15A); placing tack clamps 51 in position relative to the shield the gas nozzle 57 as shown in FIG. 15B; tack welding the weld plate 35, 135 in a plurality (e.g., ~10-15) weld spots 58 (FIG. 17A) using about 1 to about 3 J, preferably about 2 J at about 3 to about 7 msec, preferably about 5 msec; removing the clamps 51 and checking the alignment of CNC program to the IM nail 30/weld plate 35, 135 assembly; adjusting the weld path if required; fitting heat sinks 55 and re-checking weld path alignment as shown in FIGS. 16A-16B; positioning the shield gas nozzle 57 as shown in FIGS. 17B and 18; welding the IM nail 30 using the following approximate parameters: pulse energy ~2 J, pulse duration ~5 msec, pulse repletion rate ~5 Hz, traverse speed ~100 mm/min, laser focused on material surface using an 80 mm focal length lens, argon shielding gas delivered at about 20 l/min at a pressure of 3 bars with about a 6 mm diameter shield gas nozzle 57.

The weld overlap can range from about 35% to about 80% and weld penetration can range from about 40% to about 85%. A reduced overlap of about 35% and a high penetration resulted in the cavity temperatures reported in Table 1. An increased overlap between about 70 and 80% and a reduced weld penetration between about 40 and 60% reduced the cavity temperature to about 135° C. With a 200-300 μm weld spot size, the weld spots are created at 40 μm intervals. Weld overlap above 80% may cause the cavity temperature to rise above 150° C., which may damage the silicone encapsulant or require a reduced or undesirably shallow weld penetration. Of course all of the above parameters may vary depending on the IM nail design and the particular sensors being protected. A partial sectional view of a final weld test part is illustrated in FIG. 19.

Figure 19A:
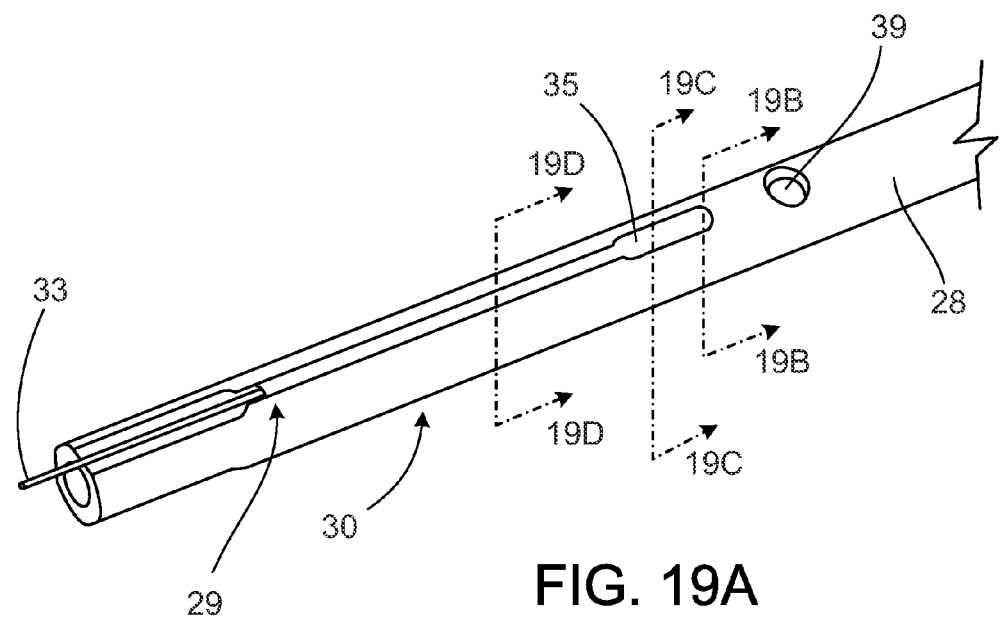
FIG. 19A is a partial perspective view of a disclosed IM nail after welding and FIGS. 19B-19D are sectional images the IM nail of FIG. 19A taken substantially along lines 19B-19B, 19C-19C and 19D-19D respectively.
Figure 19B:
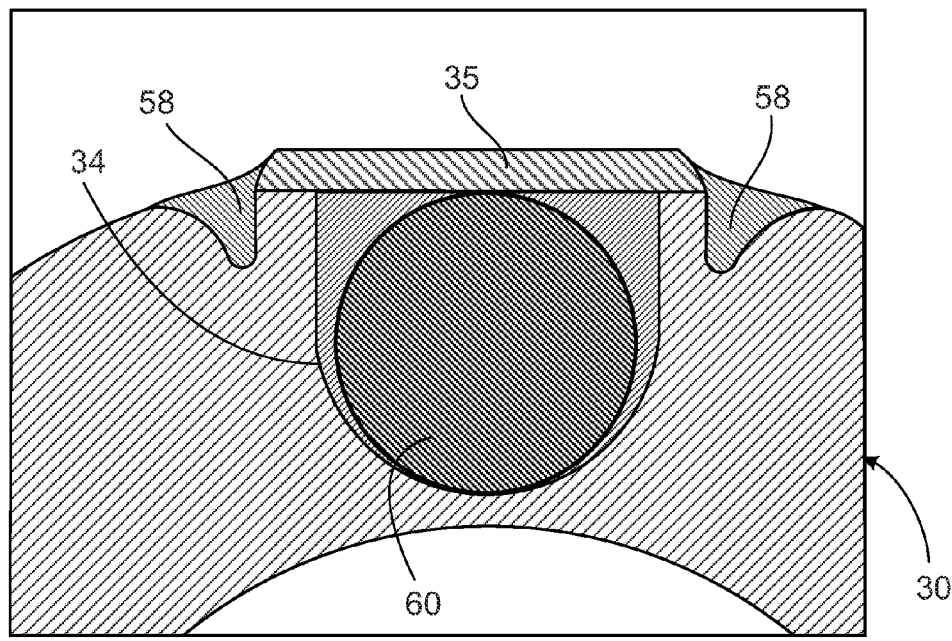
Figure 19C:
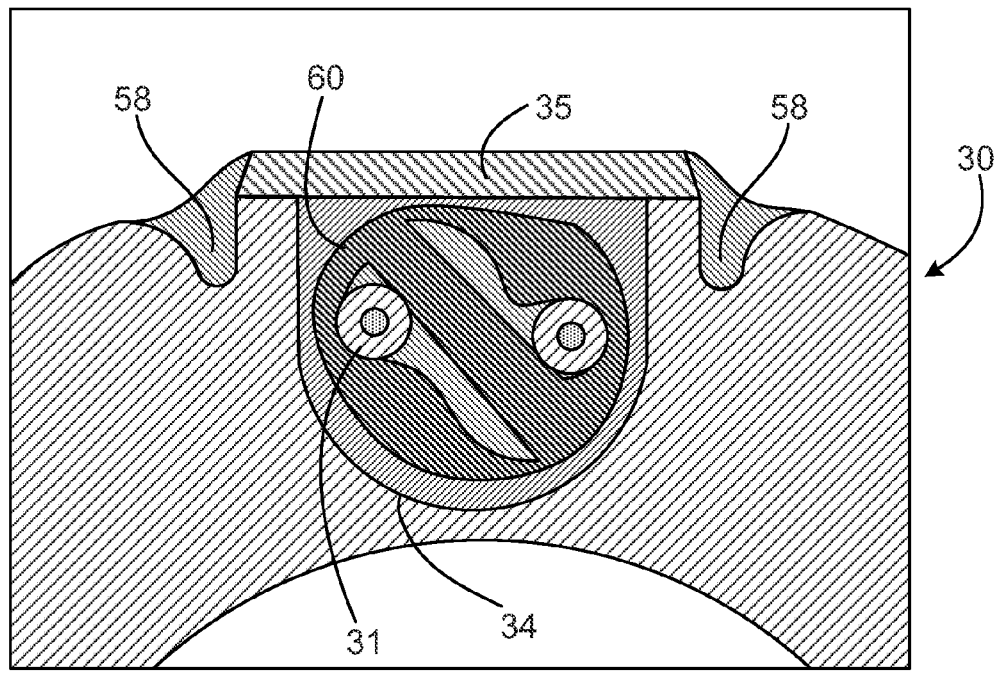
Figure 19D:
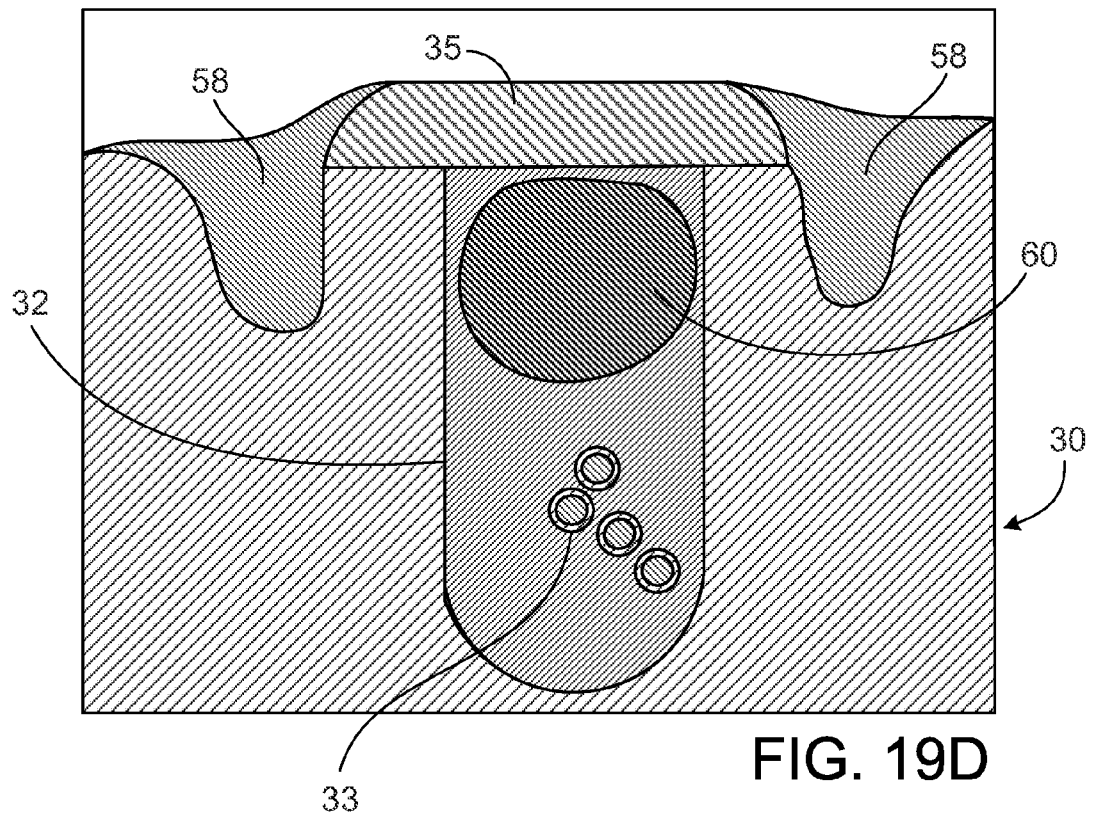

FIGS. 19A-19D show sectional images of a hermetically sealed sensor 31, wire bus 33, weld plate 35 and encapsulant 60. In FIG. 19B, the sensor 31 is not clearly visible but the offset between the cavity 34 and weld spots 58 is shown. In FIG. 19C, a sectional view of the sensor 31 embedded in the encapsulant 60 is shown. In FIG. 19D, a sectional view of the wire bus 33, channel 32 and weld plate 35 is shown.

While only certain embodiments have been set forth, alternatives and modifications will be apparent from the above description to those skilled in the art. These and other alternatives are considered equivalents and within the spirit and scope of this disclosure and the appended claims.

The invention claimed is:

1. A method for hermetically sealing an electronic component in a load-bearing implant, the method comprising:

providing a load-bearing implant with a cavity for accommodating the electronic component, the load-bearing implant defining an inner bore;

providing a weld plate configured to cover the cavity with an offset margin extending around a periphery of the cavity;

encapsulating the electronic component in the cavity within an encapsulant;

curing the encapsulant at a first temperature;

heat treating the cured encapsulant to a second temperature;

placing a heat sink in the inner bore of the load-bearing implant; and while the heat sink is located in the inner bore of the load-bearing implant, welding the weld plate over the cavity along the offset margin so the weld plate provides a seal over the cavity.

2. The method of claim 1 wherein providing the load-bearing implant comprises providing an implant defining a channel in an outer surface, the channel extending from the cavity and along the outer surface of the implant, the electronic component is connected to at least one wire, the at least one wire extends through the channel;

wherein the encapsulating comprises forming a barrier that prevents body fluids from entering the cavity and reaching the electronic component; and wherein the welding comprises welding the weld plate over at least a portion of the channel as well as the cavity without causing thermal damage to the encapsulant.

3. The method of claim 2 wherein the encapsulating comprises encapsulating the electronic component in the cavity within a silicone encapsulant that is temperature stable below about 150° C.; and wherein the welding comprises welding the weld plate over the cavity and the channel such that the welding of the weld plate does not result in temperatures of the encapsulant reaching 150° C. or above.

4. The method of claim 3 wherein the encapsulating comprises filling the channel and the cavity with the silicone encapsulant without leaving void spaces.

5. The method of claim 3 wherein the encapsulating comprises encapsulating the electronic component in the cavity within a two-component silicone.

6. The method of claim 1 wherein the welding comprises welding the weld plate over the cavity using pulsed laser energy in the range of from about 1 to about 3 J.

7. The method of claim 1 wherein the welding comprises welding the weld plate over the cavity using laser pulses having a duration of from about 2 to about 8 msec.

8. The method of claim 1 wherein the welding comprises welding the weld plate over the cavity using laser pulses repeated at a rate of from about 2 to about 8 Hz.

9. The method of claim 1 wherein the welding comprises welding the weld plate over the cavity using a traverse speed in the range of from about 50 to about 150 mm/min.

10. The method of claim 1 wherein the welding comprises overlapping weld spots generated by a pulsed laser by an amount ranging from about 35 to about 80%.

11. The method of claim 1 wherein the welding comprises using a pulsed laser that generates weld spots having a weld penetration ranging from about 40 to about 85%.

12. The method of claim 1 wherein the welding comprises using a pulsed laser with welding parameters comprising a pulse energy of about 2 J, a pulse duration of about 5 msec, a pulse repetition of about 5 Hz and a traverse speed of about 100 mm/min.

13. The method of claim 1 wherein the welding comprises using a pulsed laser with welding parameters comprising a pulse energy of about 2 J, a pulse duration of about 5 msec, a pulse repetition of about 5 Hz, a traverse speed of about 100 mm/min, a weld overlap ranging from about 35 to about 80%, and a weld penetration ranging from about 40 to about 85%.

14. The method of claim 1 wherein providing the load-bearing implant comprises providing a load-bearing implant in which an outer surface defining the cavity is metallic.

15. The method of claim 1 further comprising coupling a second heat sink to the implant.

16. The method of claim 15 wherein coupling the second heat sink to the implant comprises coupling to the implant a heat sink comprising an external sleeve with an aperture that surrounds the cavity and the offset margin.

17. The method of claim 1 wherein the second temperature is greater than the first temperature.

18. The method of claim 1, wherein providing the load-bearing implant comprises providing a load-bearing implant having a proximal end, a distal end, and an outer surface that extends along a longitudinal extent of the load-bearing implant between the proximal end and the distal end, the cavity having an opening defined in the outer surface, the opening extending along a portion of the longitudinal extent of the load-bearing implant; and wherein welding the weld plate over the cavity comprises welding the weld plate over the opening of the cavity.

19. The method of claim 18, wherein providing the load-bearing implant comprises providing a load-bearing implant defining a longitudinal channel in the outer surface adjacent the opening of the cavity; and wherein welding the weld plate comprises welding the weld plate over the opening of the cavity and a portion of the channel along the offset margin without causing substantial thermal damage to the encapsulant, the weld plate forming a seal over the cavity and the portion of the channel.

20. The method of claim 18, wherein providing the load-bearing implant comprises providing an intramedullary nail that defines the channel in the outer surface from the opening of the cavity to the proximal end of the intramedullary nail.

21. The method of claim 1, further comprising, after encapsulating the electronic component in the cavity within the encapsulant, placing a clamp configured to mold a surface of the encapsulant over the opening of the cavity; and wherein curing the encapsulant comprises curing the encapsulant with the clamp located over the opening of the cavity.

22. The method of claim 1, further comprising, after encapsulating the electronic component in the cavity within the encapsulant and before curing the encapsulant:

placing the load-bearing implant in a pressurization chamber; and performing one or more vacuum cycles that decrease the pressure in the pressurization chamber below atmospheric pressure.

23. The method of claim 1, further comprising, after encapsulating the electronic component in the cavity within the encapsulant and before curing the encapsulant:

placing the load-bearing implant in a pressurization chamber; and performing one or more pressurization cycles that increase pressure in the pressurization chamber above atmospheric pressure.

24. A method for hermetically sealing an electronic component in a load-bearing implant, the method comprising:

providing a load-bearing implant with a cavity for accommodating the electronic component, the cavity having a length, a width, and a depth, wherein the length is greater than the width and the depth;

providing a weld plate configured to cover the cavity with an offset margin extending around a periphery of the cavity;

encapsulating the electronic component in the cavity within a silicone encapsulant;

curing the silicone encapsulant at a first temperature;

heat treating the cured silicone encapsulant to a second temperature; and welding the weld plate over the cavity at the offset margin in a direction along the length of the cavity to form a seal over the cavity.

25. A method for hermetically sealing an electronic component in a load-bearing implant, the method comprising:

providing a load-bearing implant with a cavity for accommodating the electronic component;

providing a weld plate configured to cover the cavity with an offset margin extending around a periphery of the cavity;

encapsulating the electronic component in the cavity within an encapsulant;

after encapsulating the electronic component in the cavity within the encapsulant, subjecting the load-bearing implant to (i) one or more vacuum cycles that expose the load-bearing implant to pressure below atmospheric pressure, or (ii) one or more pressurization cycles that expose the load-bearing implant to pressure above atmospheric pressure;

curing the encapsulant at a first temperature;

heat treating the cured encapsulant to a second temperature; and welding the weld plate over the cavity along the offset margin so the weld plate provides a seal over the cavity.

26. The method of claim 24, wherein providing the load-bearing implant comprises providing an orthopaedic implant defining a proximal opening, a distal opening, and an interior cannulation extending from the proximal opening to the distal opening, the orthopaedic implant having a wall disposed between the interior cannulation and an outer surface of the orthopaedic implant, wherein the cavity is positioned in and defined in part by the outer surface and the wall of the orthopaedic implant and is disposed between the proximal opening and the distal opening; and wherein welding the weld plate over the cavity comprises welding along the offset margin at locations between the proximal opening and the distal opening.

27. The method of claim 24, further comprising selecting welding parameters for achieving a weld penetration within a predetermined range;

wherein welding the weld plate over the cavity comprises applying pulsed laser energy along the offset margin according to the selected welding parameters to create a weld having a weld penetration within the predetermined range.

28. The method of claim 27, wherein selecting the welding parameters comprises selecting parameters that achieve a weld penetration between 30% and 85%, the selected parameters including a pulse energy, a pulse duration, and a weld overlap.

29. The method of claim 28, wherein selecting the welding parameters comprises:

selecting a pulse energy between about 1 J to about 3 J;

selecting a pulse duration between about 2 milliseconds and about 8 milliseconds; and selecting a weld overlap between about 35% and 80%.

30. The method of claim 24, further comprising, while welding the weld plate over the cavity, applying a shield gas to the load-bearing implant or the weld plate.

31. The method of claim 30, wherein applying a shield gas to the load-bearing implant comprises applying the shield gas at a rate between about 10 liters/minute to about 30 liters/minute at a pressure between about 2 bar to about 4 bar.

* * * * *